US008148102B2

(12) United States Patent
Cheng

(10) Patent No.: US 8,148,102 B2
(45) Date of Patent: Apr. 3, 2012

(54) SEQUENCES FOR FK228 BIOSYNTHESIS AND METHODS OF SYNTHESIZING FK228 AND FK228 ANALOGS

(75) Inventor: Yi-Qiang Cheng, Grafton, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 88 days.

(21) Appl. No.: 12/526,202

(22) PCT Filed: Feb. 8, 2008

(86) PCT No.: PCT/US2008/053473
§ 371 (c)(1),
(2), (4) Date: Aug. 6, 2009

(87) PCT Pub. No.: WO2008/098199
PCT Pub. Date: Aug. 14, 2008

(65) Prior Publication Data
US 2010/0261878 A1    Oct. 14, 2010

Related U.S. Application Data

(60) Provisional application No. 60/888,851, filed on Feb. 8, 2007.

(51) Int. Cl.
C12P 1/00 (2006.01)
C12P 21/02 (2006.01)
(52) U.S. Cl. .................... 435/41; 435/71.3
(58) Field of Classification Search ............ None
See application file for complete search history.

(56) References Cited

U.S. PATENT DOCUMENTS

| 4,977,138 | A * | 12/1990 | Okuhara et al. ............... 514/2.9 |
| 6,828,302 | B1 | 12/2004 | Skov |
| 7,153,667 | B2 | 12/2006 | Shen et al. |
| 2003/0186388 | A1* | 10/2003 | Ueda et al. .................... 435/71.2 |
| 2006/0106049 | A1 | 5/2006 | Odenike |
| 2006/0128660 | A1 | 6/2006 | Rajski et al. |
| 2011/0060021 | A1 | 3/2011 | Cheng et al. |

FOREIGN PATENT DOCUMENTS

| JP | 3141296 | 6/1991 |
| JP | 2006136291 | 6/2006 |
| WO | WO 2008/098199 | 8/2008 |
| WO | WO 2009/022182 | 2/2009 |
| WO | WO 2010/116173 | 10/2010 |

OTHER PUBLICATIONS

Acharya, M.R. et al., "Rational development of histone deacetylase inhibitors as anticancer agents: a review," Mol. Pharmacol. (2005) 68:917-932.

(Continued)

Primary Examiner — Nashaat Nashed
(74) Attorney, Agent, or Firm — Michael Best & Friedrich LLP

(57) ABSTRACT

Polynucleotides encoding the polypeptides involved in biosynthesis of FK 228 and those involved in synthesis of a novel FK228 analog, thailandepsin are disclosed herein. Also provided are methods of making FK228, thailandepsin and analogs of these molecules and methods of using these FK228 analogs. *Chromobacterium* and *Burkholderia* gene inactivation mutants are provided. Methods of forming a disulfide bond in a chemical are also disclosed.

10 Claims, 9 Drawing Sheets

OTHER PUBLICATIONS

Allis et al., "New nomenclature for chromatin-modifying enzymes," Cell (2007) 131:633-636.

Altschul, S.f. et al., "Basic local alignment search tool," J. Mol. Biol. (1990) 215:403-410.

Ansari, M.Z. et al., "NRPS-PKS: a knowledge-based resource for analysis of NRPS/PKS megasynthases," Nucl. Acids Res. (2004) 32:W405-413.

Balasubramanian, S. et al., "Isoform-specific histone deacetylase inhibitors: the next step?" Cancer Lett. (2009) 280:211-221.

Bernstein, B.e. et al., "The mammalian epigenome," Cell (2007) 128:669-681.

Bolden, J.E. et al., "Anticancer activities of histone deacetylase inhibitors," Nat. Rev. Drug Disc. (2006) 5(9):769-784.

Brazilian National Genome Project Consortium, "The complete genome sequence of *Chromobacterium violaceum* reveals remarkable and exploitable bacterial adaptability," Proc. Natl. Acad. Sci. USA (2003) 100:11660-11665.

Brett, P.J. et al., "*Burkholderia thailandensis* sp. Nov., a *Burkholderia pseudomalles*-like species," Intl. J. Systemic Bacteriology (1998) 48:317-320.

Byrd, J.C. et al., "A phase 1 and pharmacodynamic study of depsipeptide (FK228) in chronic lymphoccytic leukemia and acute myeloid leukemia," Blood (2005) 105:959-967.

Byrd, J.C. et al., "Depsipeptide (FR901228): a novel therapeutic agent with selective, in vitro activity against human B-cell chronic lymphocytic leukemia cells," Blood (1999) 94:1401-1408.

Challis, G.L. et al., "Predictive, structure-based model of amino acid recognition by nonribosomal peptide synthetase adenylation domains," Chem. Biol. (2000) 7:211-224.

Cheng, Y. "Deciphering the biosynthetic codes for the potent anti-SARS-CoV cyclodepsipeptide valinomycin in *Streptomyces tsusimaensis* ATCC 15141," Chem Bio Chem. (2006) 7:471-477.

Cheng, Y.Q. et al., "Type I polyketide synthase requiring a discrete acyltransferase for polyketide biosynthesis," Proc. Natl. Acad. Sci. USA (2003) 100:3149-3154.

Cheng, Y-Q et al., "Characterization of a gene cluster responsible for the biosynthesis of anticancer agent FK228 in *Chromobacterium violaceum* No. 968," App. Environ. Microbiol. (2007) 73(11):3460-3469.

Cheng, Y.Q., et al., "Type I polyketide syntheses that require discrete acyltransferases," Methods in Enzymol. (2009) 459:165-186.

Corre, C. et al., "New natural product biosynthetic chemistry discovered by genome mining," Nat. Prod. Rep. (2009) 26:977-986.

Database UniProt [online] "SubName: Full=Acyl-CoA dehydrogenase domain protein," (Jan. 24, 2006) Retrieved from EBI accession No. UNIPROT:Q2SW16, 3 pages.

De Rujiter, A.J.M. et al., "Histone deacetylases (HDACs): characterization of the classical HDAC family," Biochem. J. (2003) 370:737-749.

Dokmanovic, M. et al., "Prospects: histone deacetylase inhibitors," J. Cell Biochem. (2005) 96:293-304.

Donadio, S. et al., "Polyketide synthases and nonribosomal peptide synthetases: the emerging view from bacterial genomics," Nat. Prod. Rep. (2007) 24:1073-1109.

Duitman, E.H. et al., "The mycosubtilin synthetase of *Bacillus subtilis* ATCC6633: a multifunctional hybrid between a peptide synthetase, an amino transferase, and a fatty acid synthase," Proc. Natl. Acad. Sci. USA (1999) 96:13294-13299.

Duran, N. et al., "*Chromobacterium violaceum*: a review of pharmaological and industrial perspectives," Crit. Rev. Microbiol. (2001) 27:201-222.

Finan, T.M. et al., "Second symbiotic megaplasmid in *Rhizobium meliloti* carrying exopolysaccharide and thiamine synthesis genes," J. Bacteriol. (1986) 167:66-72.

Finking, R. et al., "Biosynthesis of nonribosomal peptides," Annu. Rev. Microbiol. (2004) 58:453-488.

Finnin, M.S. et al., "Structures of a histone deacetylase homologue bound to the TSA and SAHA inhibitors," Nature (1999) 401:188-193.

Fischbach, M.A. et al., "Assembly-line enzymology for polyketide and nonribosomal peptide antibiotics: logic, machinery, and mechanisms," Chem. Rev. (2006) 106:3468-3496.

Furumai, R. et al., "FK228 (depsipeptide) as a natural prodrug that inhibits class I histone deacetylases," Cancer Res. (2002) 62:4916-4921.

Garber, K., "HDAC inhibitors overcome first hurdle," Nat. Biotech. (2007) 25:17-19.

Gehring, A.M. et al., "Iron acquisition in plague: modular logic in enzymatic biogenesis of yersiniabactin by *Yersinia pestis*," Chem. Biol. (1998) 5:573-586.

Grunewald, J. et al., "Chemoenzymatic and template-directed synthesis of bioactive macrocyclic peptides," Microbiol. Mol. Biol. Rev. (2006) 70:121-146.

Halili, M.A. et al., "Histone deacetylase inhibitors in inflammatory disease," Curr. Top. Med. Chem. (2009) 9(3):309-319.

He, B. et al., "Binding ensemble profiling with photoaffinity labeling (BEProFL) approach: mapping the binding poses of HDAC8 inhibitors," J. Med. Chem. (2009) 52:7003-7013.

Heathcote, M.L. et al., "Role of type II thioesterases: evidence for removal of short acyl chains produced by aberrant decarboxylation of chain extender units," Chem. Biol. (2001) 8:207-220.

Hill, A.M., "The biosynthesis, molecular genetics and enzymology of the polyketide-derived metabolites," Nat. Prod. Rep. (2006) 23:256-320.

Hoang, T.t. et al., "A broad-host-range Flp-FRT recombination system for site-specific excision of chromosomally-located DNA sequences: application for isolation of unmarked *Pseudomonas aeruginosa* mutants," Gene (1998) 212:77-86.

Holbeck, S.L. et al., "Analysis of Food & Drug Administration—Approved anticancer agents in the NC160 panel of human tumor cell lines," Mol. Cancer Ther. (2010) 9:1451-1460.

Hutt, D.M. et al., "Reduced histone deacetylase 7 activity restores function to misfolded CFTR in cystic fibrosis," Nat. Chem. Biol. (2010) 6:25-33.

Johnstone, R.W., "Histone-deacetylase inhibitors: novel drugs for the treatment of cancer," Nat. Rev. Drug Discov. (2002) 1:287-299.

Kazantsev, A.G. et al., "Therapeutic application of histone deacetylase inhibitors for central nervous system disorders," Nat. Rev. Drug Discov. (2008) 7(10):854-868.

Kieser, T. et al., "Practical *Streptomyces* genetics," John Innes Foundation, Norwich England (2000) cover and table of contents.

Kim, H.S. et al., Bacterial genome adaption to niches: divergence of the potential virulence genes in three *Burkholderia* species of different survival strategies, BMC Genomics (2005) 6:174, 13 pages.

Kim, H.S. et al., Database EMBL [online] "*Burkholderia thailandensis* E264 chromosome I, complete sequence," (Jan. 18, 2005) Retrieved from EBI accession No. EMBL:CP000085, 1 page.

Lambalot, R.H. et al., "A new enzyme superfamily—the phosphopantetheinyl transferases," Chem. Biol. (1996) 3:923-936.

Lane, A.A. et al., "Histone deacetylase inhibitors in cancer therapy," J. Clin. Oncol. (2009) 27:5459-5468.

Lee, C. et al., "A highly specific D-hydroxyisovalerate dehydrogenase from the enniatin producer *Fusarium sambucinum*," J. Biol. Chem. (1992) 267:11741-11744.

Li, M.H.T. et al., "Automated genome mining for natural products," BMC Bioinformatics (2009) 10:185, 10 pages.

Li, K.W. et al., "Total synthesis of the antitumor depsipeptide FR-901,228," J. Am. Chem. Soc. (1996) 118:7237-7238.

Ma, W.W. et al., "Novel agents on the horizon for cancer therapy," Ca Cancer J. Clin. (2009) 59(2):111-137.

Ma, X. et al., "Histone deacetylase inhibitors, current status and overview of recent clinical trials," Drugs (2009) 69:1911-1934.

MacNeil, D.J. et al., "Analysis of *Streptomyces avermitilis* genes required for avermectin biosynthesis utilizing a novel integration vector," Gene (1992) 61-68.

Magarvey, N.A. et al., "Characterization of the cereulide NRPS alpha-hydroxy acid specifying modules: activation of alpha-keto acids and chiral reduction on the assembly line," J. Am. Chem. Soc. (2006) 128:10698-10699.

Mai, A. et al., "Histone deacetylases inhibitors and neurodegenerative disorders: holding the promise," Curr. Pharm. Des. (2009) 15(34):3940-3957.

Mai, A. et al., "Identification of two new synthetic histone deacetylase inhibitors that modulate globin gene expression in erythroid cells from healthy donors and patients with thalassemia," Mol. Pharmacol. (2007) 72(5):1111-1123.

Mann, B.S. et al., "FDA approval summary: vorinostat for treatment of advanced primary cutaneous T-cell lymphoma," The Oncologist (2007) 12:1247-1252.

Marshall, J.L. et al., "A phase I trial of depsipeptide (FR901228) in patients with advanced cancer," J. Exp. Ther. Oncol. (2002) 2:325-332.

Masuoka, Y. et al., "Spiruchostatins A and B, novel gene expression-enhancing substances produced by Pseudomonas sp," Tetrahedron Lett. (2001) 42:41-44.

McAlpine, J.B. et al., "Microbial genomics as a guide to drug discovery and structural elucidation: ECO-02301, a novel antifungal agent, as an example," J. Nat. Prod. (2005) 68:493-496.

Monga, M. et al., "Developmental therapeutics program at the NCI: molecular target and drug discovery process," Leukemia (2002) 16:520-526.

Monneret, C., "Histone deacetylase inhibitors," Eur. J. Med. Chem. (2005) 40:1-13.

Mootz, H.D. et al., "Ways of assembling complex natural products on modular nonribosomal peptide synthetases," Chembiochem. (2002) 3:490-504.

Nakajima, H. et al., "FR901228, a potent antitumor antibiotic, is a novel histone deacetylase inhibitor," Exp. Cell Res. (1998) 241:126-133.

Ng, P.C. et al., "Whole genome sequencing," Methods Mol. Biol. (2010) 628:215-226.

Ochman, H. et al., "Lateral gene transfer and the nature of bacterial innovation," Nature (2000) 405:299-304.

Oikawa, H. et al., Database EMBL [online] "*Streptomyces lasaliensis* gene cluster(ecm1, ecm2, ecm3, ecm4, ecm5, ecm6, ecm7, ecm8, ecm9, ecm10, ecm11, ecm12, ecm13, ecm14, ecm15, ecm16, ecm17, ecm18), complete eds," (Jul. 21, 2006) Retrieved from EBI accession No. EMBL:AB211309, 18 pages.

Piekarz, R. et al., "A review of depsipeptide and other histone deacetylase inhibitors in clinical trials," Curr. Pharm. Des. (2004) 10:2289-2298.

Piekarz, R.L. et al., "Inhibitor of histone deacetylation depsipeptide (FR901228) in the treatment of peripheral and cutaneous T-cell lymphoma: a case report," Blood (2001) 98:2865-2868.

Piekarz, R.L. et al., "Epigenetic modifiers: basic understanding and clinical development," Clin. Cancer Res. (2009) 15(12):3918-3926, 3947-3977.

Piel, J., "A polyketide synthase-peptide synthetase gene cluster from an uncultured bacterial symbiont of Paederus beetles," Proc. Natl. Acad. Sci. USA (2002) 99:14002-14007.

Potharla, V.Y. et al., "New insights into the genetic organization of the FK228 biosynthetic gene cluster in *Chromobacterium violaceum* No. 968," Appl. Environ. Microbiol. (2011) 77(4):1508-1511.

Rajgolikar, G. et al., "Effects of a novel antitumor depsipeptide, FR901228, on human breast cancer cells," Breast Cancer Res. Treat. (1998) 51:29-38.

Reeves, C.D. et al., "Alteration of the substrate specificity of a modular polyketide synthase acyltransferase domain through site-specific mutations," Biochem. (2001) 40:15464-15470.

Rotili, D. et al., Non-cancer uses of histone deacetylase inhibitors: effects on infectious diseases and B-hemoglobinopathies, Curr. Top. Med. Chem. (2009) 9(3):272-291.

Sandor, V. et al., "FR901228 causes mitotic arrest but does not alter microtubule polymerization," Anticancer Drugs (2000) 11:445-454.

Sandor, V. et al., "P21-dependent g(1) arrest with downregulation of cyclin D1 and upregulation of cyclin E by the histone deacetylase inhibitor FR901228," Br. J. Cancer (2000) 83:817-825.

Sandor, V. et al., "Phase I Trial of the histone deacetylase inhibitor, depsipeptide (FR901228, NSC 630176), in patients with refractory neoplasms," Clin. Cancer Res. (2002) 8:718-728.

Shen, B., "Polyketide biosynthesis beyond the type I, II and III polyketide synthase paradigms," Curr. Opin. Chem. Biol. (2003) 7:285-295.

Shigematsu, N. et al., "FR901228, a novel antitumor bicyclic depsipeptide produced by *Chromobacterium violaceum* No. 968. II. Structure determination," J. Antibiot. (Tokyo) (1994) 47:311-314.

Shoemaker, R.H., "The NCI60 human tumour cell line anticancer drug screen," Nat. Rev. Cancer (2006) 6(11):813-823.

Stachelhaus, T. et al., "The specificity-conferring code of adenylation domains in nonribosomal peptide synthetases," Chem. Biol. (1999) 6:493-505.

Stat Bite: FDA Oncology Drug Product Approvals in 2009, J. Natl. Cancer Inst. (2010) 102:219.

Straight, P.D. et al., "A singular enzymatic megacomplex from *Bacillus subtilis*," Proc. Natl. Acad. Sci. USA (2007) 104:305-310.

Thomas, M.G. et al., "Deciphering tuberactinomycin biosynthesis: isolation, sequencing, and annotation of the viomycin biosynthetic gene cluster," Antimicrob. Agents Chemother. (2003) 47:2823-2830.

Tsuge, K. et al., "Cloning, sequencing and characterization of the iturin A operon," J. Bacteriol. (2001) 183:6265-6273.

Ueda, H. et al., "Action of FR901228, a novel antitumor bicyclic depsipeptide produced by *Chromobacterium violaceum* No. 968, on Ha-ras transformed NIH3T3 cells," Biosci. Biotech. Biochem. (1994) 58:1579-1583.

Ueda, H. et al., "FR901228, a novel antitumor bicyclic depsipeptide produced by *Chromobacterium violaceum* No. 968 1. Taxonomy, fermentation, isolation, physico-chemical and biological properties, and antitumor activity," J. Antibiotics (1994) 47(3):301-310.

Ueda, H. et al., "FR901228, a novel antitumor bicyclic depsipeptide produced by *Chromobacterium violaceum* No. 968. III. Antitumor activities on experimental tumors in mice," J. Antibiot. (1994) 47(3):315-323.

Vigushin, D.M., "FR-901228 Fujisawa/National Cancer Institute," Curr. Opin. Invest. Drugs (2002) 3:1396-1402.

Walsh, C.T., "Combinatorial biosynthesis of antibiotics: challenges and opportunities," Chembiochem. (2002) 3:125-134.

Walsh, C.T., "Polyketide and nonribosomal peptide antibiotics: modularity and versalitity," Science (2004) 303:1805-1810.

Wang, C. et al., "An FAD-dependent pyridine nucleotide-disulfide oxidoreductase is involved in disulfide bond formation in FK228 anticancer depsipeptide," Chem. Biol. (2009( 16(6):585-593.

Wang, H. et al., "New patented histone deacetylase inhibitors," Expert Opinion on Therapeutic Patents (2009) 19(12):1727-1757.

Watanabe, K. et al., "Total biosynthesis of antitumor nonribosomal peptides in *Escherichia coli*," Nature Chem. Biol. (2006) 2(8):423-428.

Wegener, D. et al., "Improved fluorogenic histone deacetylase assay for high-throughput-screening applications," Anal. Biochem. (2003) 321:202-208.

Wenzel, S.C. et al., "Formulation of novel secondary metabolites by bacterial multimodular assembly lines: deviations from textbook biosynthetic logic," Curr. Opin. Chem. Biol. (2005) 9:447-458.

Wesener, S.R. et al., "Reconstitution of FK228 biosynthetic pathway revealing cross-talk between modular polyketide synthases and fatty acid synthase," Appl. Environ. Microbiol. (2011) 77:1501-1507.

Xiao, J.J. et al., "Identification of thiols and glutathioine conjugates of depsipeptide FK228 (FR901228) a novel histone protein deacetylase inhibitor, in the blood," Rapid Commun. Mass Spectrom. (2003) 17:757-766.

Yoo, C.B. et al., "Epigenetic therapy of cancer: past, present and future," Nat. Rev. Drug. Discov. (2006) 5:37-50.

Yurek-George, A. et al., "The first biologically active synthetic analogues of FK228, the depsipeptide histone deacetylase inhibitor," J. Med. Chem. (Oct. 24, 2007) 7 pages.

Zazopoulos, E. et al., "A genomics-guided approach for discovering and expressing cryptic matabolic pathways," Nat. Biotech. (2003) 21:187-190.

International Search Report and Written Opinion for Application No. PCT/US2008/053473 dated Jan. 13, 2009 (24 pages).

* cited by examiner (a)

(b)

```
 41   V L E F F S F F C P H C Y Q F E E V - - - - L H I S D N V K   Ec_DsbA.PRO
 41   V L E F F S F Y C P H C Y Q F E E V - - - - L H V S D N V K   St_DsbA.PRO
153   R W G R S V Y H C P Y C H G Y E L N E G R I G V L G - N G S   Bt_TdpH.PRO
148   R W G E S V F H C P Y C H G Y E L D G G R I G V L G - S G P   Cv_DepH.PRO
130   C W G R S V I H C P F C L G E E N A G G S W A T L A D N A H   Sl_Ecm17.PRO
```

SEQUENCES FOR FK228 BIOSYNTHESIS AND METHODS OF SYNTHESIZING FK228 AND FK228 ANALOGS

CROSS-REFERENCE TO RELATED APPLICATIONS

This application is a national stage filing under 35 U.S.C. 371 of International Application No. PCT/US2008/053473, filed on Feb. 8, 2008, which claims priority to U.S. Provisional Application No. 60/888,851, filed Feb. 8, 2007, which are incorporated herein by reference in their entireties.

STATEMENT REGARDING FEDERALLY SPONSORED RESEARCH

None.

SEQUENCE LISTING

This application contains a sequence listing. The nucleotide and amino acid sequences listed in Appendix A, Appendix B and Appendix C are incorporated herein by reference in their entireties.

BACKGROUND

Histone deacetylase (HDAC) inhibitors are a diverse group of molecules that can induce growth arrest, differentiation, apoptosis and autophagocytic cell death of cancer cells. Hence, HDAC inhibitors are prime agents for the development of novel anticancer drugs. One HDAC inhibitor, Zolinza (vorinostat or suberoylanilide hydroxamic acid—SAHA), was recently approved by the U.S. Food and Drug Administration, and at least nine other HDAC inhibitors, including FK228, are in various stages of clinical trials.

FK228 ($C_{24}H_{36}N_4O_6S_2$; molecular weight, 540.2) (FIG. 1), also known as FR901228 or depsipeptide and registered as NSC 630176 or romidepsin, is a natural product discovered in the fermentation broth of *Chromobacterium violaceum* No. 968 in a screening program for agents that reverse the malignant phenotype of a Ha-ras oncogene-transformed NIH 3T3 cell line (Ueda, Nakajima et al. 1994; Ueda, Nakajima et al. 1994). FK228 exhibits anticancer activities against an array of tumor cell lines, including many members of a standard panel of 60 cell lines from the U.S. National Cancer Institute (Vigushin 2002; Garber 2007). In clinical trials, FK228 has shown promise as an anticancer drug (NCI 2008).

Structurally, FK228 is a bicyclic depsipeptide that features a 16-membered macrolactone ring containing an ester linkage and a 17-membered ring containing the same ester linkage and a disulfide bond (FIG. 1). Its structure was determined by spectroscopic and X-ray crystallographic analyses (Shigematsu, Ueda et al. 1994) and was confirmed by total synthesis (Li, Wu et al. 1996). Its intramolecular disulfide bond makes FK228 structurally distinct from other known HDAC inhibitors, such as hydroxamic acids, apicidin and trapoxin. FK228 serves as a stable prodrug that is converted to its active form by intracellular reduction of the disulfide bond after uptake into the cells or organisms. The freed sulfhydryl group on the longer aliphatic tail of reduced FK228 fits inside the catalytic pocket of preferred class I HDACs, chelating $Zn^{2+}$, thus inhibiting HDAC activity (Furumai, Matsuyama et al. 2002).

Despite its promise as an anticancer agent, efforts to obtain large quantities of FK228 have been hampered because native production of FK228 from *Chromobacterium violaceum* No. 968 is relatively limited, and total synthesis of FK228 has proven difficult (Li, Wu et al. 1996). Due to its anticancer activities and novel structural characteristics, FK228 may serve as a molecular scaffold to generate structural analogs, from which additional compounds with therapeutic properties may be developed.

Thus, there is a need in the art for compositions and methods for synthesizing FK228 and FK228 analogs.

SUMMARY OF THE INVENTION

In one aspect, isolated polynucleotides are disclosed. The isolated polynucleotides comprise a coding sequence encoding a polypeptide having at least 80% amino acid identity to a protein encoded by depA (SEQ ID NO: 28), depB (SEQ ID NO: 30), depC (SEQ ID NO: 32), depD (SEQ ID NO: 34), depE (SEQ ID NO: 36), depF (SEQ ID NO: 38), depG (SEQ ID NO: 40), depH (SEQ ID NO: 42), depI (SEQ ID NO: 44), depJ (SEQ ID NO: 46), depK (SEQ ID NO: 20), depL (SEQ ID NO: 22), depM (SEQ ID NO: 24), or depN (SEQ ID NO: 26). Other isolated polynucleotides comprise a coding sequence encoding a polypeptide having at least 80% amino acid identity to a protein encoded by tdpA (SEQ ID NO: 78), tdpB (SEQ ID NO: 76), tdpC1 (SEQ ID NO: 74), tdpC2 (SEQ ID NO: 70), tdpDE1 (SEQ ID NO: 72), tdpE2 (SEQ ID NO: 64), tdpF (SEQ ID NO: 68), tdpG (SEQ ID NO: 66), tdpH (SEQ ID NO: 62), tdpI (SEQ ID NO: 60), tdpJ (SEQ ID NO: 58), tdpL, or tdpN (SEQ ID NO: 80). The isolated polynucleotides may be operably connected to a promoter.

In another aspect, polypeptides are disclosed, which have at least 80% amino acid identity to DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27). Other polypeptides disclosed have at least 80% amino acid identity to TdpA (SEQ ID NO: 79), TdpB (SEQ ID NO: 77), TdpC1 (SEQ ID NO: 75), TdpC2 (SEQ ID NO: 71), TdpDE1 (SEQ ID NO: 73), TdpE2 (SEQ ID NO: 65), TdpF (SEQ ID NO: 69), TdpG (SEQ ID NO: 67), TdpH (SEQ ID NO: 63), TdpI (SEQ ID NO: 61), TdpJ (SEQ ID NO: 59), TdpL, or TdpN (SEQ ID NO: 81). The Tdp polypeptides are homologs of the Dep polypeptides and have homologous activities.

In yet another aspect, *Chromobacterium* and *Burkholderia* gene inactivation mutants are disclosed.

In still another aspect, FK228 analog compounds are disclosed. One identified FK228 analog is thailandepsin, which has three forms. In yet another aspect, the compounds are histone deacetylase inhibitors.

In a further aspect, methods of treating a disease associated with increased histone deacetylation are provided. The methods include administering an effective amount of one of the FK228 analog compounds to a subject having the disease.

In a still further aspect, methods of reducing histone deacetylase-mediated inhibition of gene expression in a cell are provided. The methods include contacting the cell with an effective amount of a composition comprising the FK228 analog compounds.

In another aspect, methods of modifying production of FK228 in *Chromobacterium violaceum* No. 968 and production of thailandepsin in *Burkholderia thailandensis* E264. The methods include introducing at least one of the polynucleotides of the dep gene cluster (SEQ ID NO: 1) into *Chromobacterium violaceum* No. 968 or introducing at least one of the polynucleotides of the tdp gene cluster (SEQ ID NO: 2) into Burkholderia thailandensis E264. The polynucleotides are operably connected to a promoter.

In yet another aspect, methods of producing an FK228 analog comprising growing Burkholderia thailandensis E264 in medium and partially isolating the FK228 analog from the growth medium are provided.

In yet another aspect, methods of making FK228 or thailandepsin analogs in recombinant cells are provided. The methods include growing a recombinant cell comprising polynucleotides encoding proteins encoded by the dep or the tdp gene cluster (SEQ ID NOS: 1 and 2) or homologs thereof under conditions that allow synthesis of FK228 or thailandepsin analogs.

In yet another aspect, methods of making an FK228 or thailandepsin analog are provided. The methods include introducing a polynucleotide into a bacterium to produce a recombinant bacterium. The polynucleotide encodes a polypeptide that is a homolog of at least one of the proteins of the dep gene cluster (SEQ ID NO: 1) or of the tdp gene cluster (SEQ ID NO: 2). The polynucleotide is operably connected to a promoter. The recombinant bacterium is then grown under conditions that allow expression of the polynucleotide and production of the FK228 or thailandepsin analog.

In yet another aspect, methods of producing FK228 or FK228 analogs in Chromobacterium violaceum No. 968 are provided. The methods include manipulating at least one of the polynucleotides of the dep gene cluster (SEQ ID NO: 1) to produce a mutated polynucleotide and introducing the mutated polynucleotide into Chromobacterium violaceum No. 968. The polynucleotides are operably connected to a promoter.

In yet another aspect, methods of producing thailandepsin or thailandepsin analogs in Burkholderia thailandensis E264 are provided. The methods include manipulating at least one of the polynucleotides of the tdp gene cluster (SEQ ID NO: 2) to produce a mutated polynucleotide and introducing the mutated polynucleotide into Burkholderia thailandensis E264. The polynucleotides are operably connected to a promoter.

In a further aspect, a polynucleotide comprising a coding sequence encoding a polypeptide having at least 80% amino acid identity to a protein encoded by ecm17 is provided. The coding sequence for ecm17 is operably connected to a promoter.

In a still further aspect, methods of forming a disulfide bond in a chemical having at least two free thiol or sulfhydryl groups are provided. The methods include contacting the chemical with a polypeptide having at least 80% amino acid identity to a protein encoded by ecm17, depH (SEQ ID NO: 42) or tdpH (SEQ ID NO: 62). The polypeptide catalyzes formation of a disulfide bond between the two thiols.

BRIEF DESCRIPTION OF THE DRAWINGS

FIG. 2A is a physical map of clones and genes. Predicted genes within the dep gene cluster (SEQ ID NO: 1) are designated depA (SEQ ID NO: 28) to depN (SEQ ID NO: 26), and open reading frames outside of the dep gene cluster (SEQ ID NO: 1) are designated orf1 (SEQ ID NO: 14) to orf3 (SEQ ID NO: 18) and orf18 (SEQ ID NO: 48) to orf21 (SEQ ID NO: 54). FIG. 2B is the proposed model of FK288 biosynthesis by a hybrid NRPS (nonribosomal peptide synthetase)-PKS (polyketide synthase)-NRPS assembly line, including accessory activities of discrete proteins. A superscript "i" indicates that a domain is inactive; a superscript "n" indicates that a domain is nonfunctional. Inactive and nonfunctional domains are light grey. Abbreviations are as follows: AL, acyl coenzyme A ligase; KS, β-ketoacyl synthase; E, epimerase.

FIG. 3A shows the construction of gene replacement vector pYC03-58b and homologous recombination via double crossover between the vector and the bacterial chromosome to generate a mutant genotype. FIG. 3B is a photograph of a Southern analysis of the genotypes of wild-type and depD (SEQ ID NO: 34)-inactivated mutant strains of C. violaceum, using the labeled 2.6-kb insert DNA of pP4-G7 as a probe.

FIG. 7a demonstrates that the A domain in Module 4 of thailandepsin pathway appears to be able to load either an alanine or a glycine to the PCP domain in Module 7, which results in the production of thailandepsin A or B, respectively. FIG. 7b demonstrates that thailandepsin B appears to be able to undergo a spontaneous dehydration reaction to yield thailandepsin C.

DETAILED DESCRIPTION

Described herein is an alternative approach to making FK228 and FK228 analogs using pathway engineering, combinatorial biosynthesis, or chemoenzymatic synthesis.

By examining the FK228 structure, we identified the building blocks of three amino acids (D-cysteine, D-valine, and L-valine), an amino acid derivative (2,3-dehydro-2-aminobutanoic acid, Dhb; also called 2,3-dehydrothreonine, Dht) and a complex L-(S,E)-3-hydroxy-7-mercaptohept-4-enoic acid moiety that is likely built from one Cys and two $C_2$ units derived from malonyl coenzyme A (MCoA). Based on this information, we hypothesized that FK228 is a hybrid nonribosomal peptide (NRP)-polyketide (PK)-NRP.

The biosynthetic gene cluster (designated as dep for depsipeptide) responsible for FK228 biosynthesis was identified, cloned and characterized. The candidate biosynthetic genes were identified by a genome scanning approach. A gene replacement system was adapted to create targeted gene-inactivated mutant strains, and the subsequent cloning and characterization of an unusual hybrid nonribosomal peptide synthetase (NRPS)-polyketide synthase (PKS)-NRPS pathway for FK228 biosynthesis in *Chromobacterium violaceum* No. 968 was elucidated. Acquisition of the dep gene cluster (SEQ ID NO: 1) and development of an efficient genetic system will allow FK228 analogs to be generated by engineered biosynthetic strategies.

Figure 2:
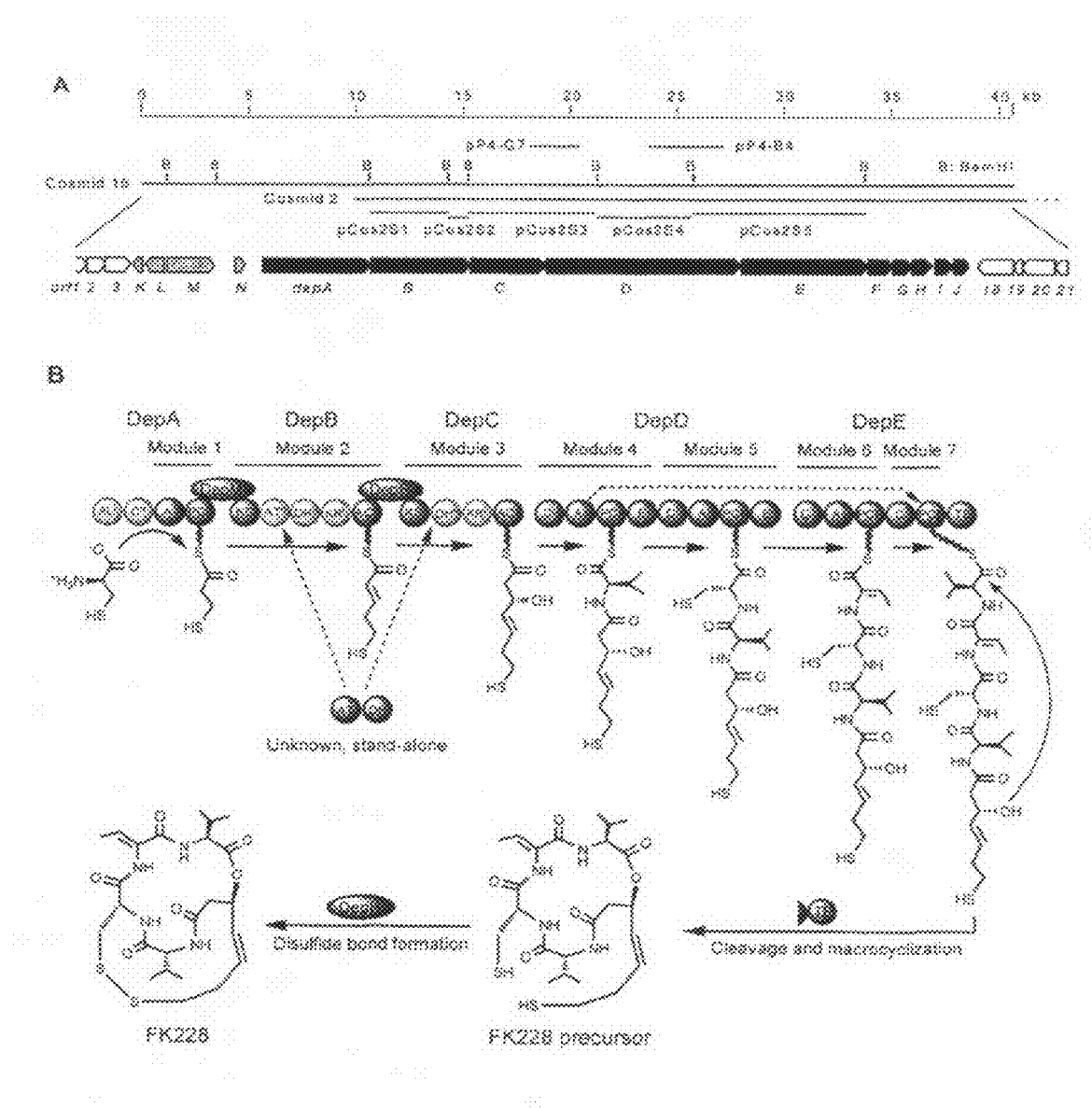
FIG. 2 depicts FK228 biosynthetic (dep) gene cluster (SEQ ID NO: 1) and a proposed model of FK228 biosynthesis.

The FK228 biosynthetic (dep) gene cluster (SEQ ID NO: 1) and a proposed model of FK228 biosynthesis are depicted in FIG. 2. The dep gene cluster (SEQ ID NO: 1) was identified by genome scanning as described in the Examples. The proposed model of FK228 biosynthesis demonstrates the roles of several of the proteins in the dep gene cluster (SEQ ID NO: 1) in FK228 biosynthesis and the pathway is described in the Examples.

The present invention encompasses isolated polynucleotides encoding a polypeptide having at least 80%, 85%, 90%, 95%, or greater amino acid identity to a protein encoded by depA (SEQ ID NO: 28), depB (SEQ ID NO: 30), depC (SEQ ID NO: 32), depD (SEQ ID NO: 34), depE (SEQ ID NO: 36), depF (SEQ ID NO: 38), depG (SEQ ID NO: 40), depH (SEQ ID NO: 42), depI (SEQ ID NO: 44), depJ (SEQ ID NO: 46), depK (SEQ ID NO: 20), depL (SEQ ID NO: 22), depM (SEQ ID NO: 24), or depN (SEQ ID NO: 26). Suitably, the polynucleotides encode DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27). The present invention also includes isolated polypeptides having at least 80%, 85%, 90%, 95%, or greater amino acid identity to DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27) and having the activity of DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27), respectively.

In another aspect, the present invention includes constructs comprising a polynucleotide of the invention operably linked to a promoter. Promoters may be any promoter active in the cell and capable of driving gene expression. Promoters include constitutive and inducible promoters. A variety of suitable promoters are known to those of skill in the art. Suitably the promoter is not the promoter natively associated with the polynucleotide. A vector comprising one or more of the polynucleotides or the polynucleotides operably connected to a promoter are also provided. Suitable vectors include, but are not limited to, a plasmid, a cosmid, a transposon, a virus, a phage, a BAC, a YAC or any other vectors known to those of skill in the art or which may be subsequently developed.

Recombinant or transgenic cells comprising one or more of the polynucleotides are provided. Such recombinant cells may be made by introducing the polynucleotides or vectors of the invention into a suitable host cell using any suitable method. Polynucleotides may be introduced into a suitable host cell by any means, including but not limited to, transformation, transduction, conjugation and electroporation. Many suitable host cells are known to those of skill in the art, including but not limited to, eukaryotic cells and prokaryotic cells. For example, recombinant or transgenic cells may be made by introducing the polynucleotides into a bacterium of a genus selected from *Chromobacterium*, *Pseudomonas*, *Escherichia*, *Salmonella*, *Burkholderia*, *Bifidobacterium*, and *Clostridium*, or in any other bacterium. Suitably the cell is capable of large scale culture or fermentation.

It is envisioned that FK228 biosynthesis by a *Chromobacterium violaceum* strain natively comprising the FK228 biosynthetic pathway, for example *Chromobacterium violaceum* No. 968, could be enhanced by introducing exogenous sequences encoding one or more proteins of the FK228 biosynthetic pathway. In other words, using the teachings of this application, one of skill in the art could readily develop *Chromobacterium violaceum* strains genetically engineered to have increased expression of one or more sequences (i.e., protein or mRNA) of the FK228 biosynthetic pathway, and such strains would reasonably be expected to have advantageous properties, such as increased FK228 biosynthesis. For example, depL (SEQ ID NO: 22) is a regulatory gene. One of skill in the art would expect that altering expression of depL (SEQ ID NO: 22) would alter expression of other dep constituents.

The FK228 biosynthetic pathway could be reconstituted in a bacterium that does not ordinarily synthesize FK228 analogs. As indicated above, bacteria that do not natively possess the FK228 biosynthetic pathway, for example, *Chromobacterium violaceum* strains other than *Chromobacterium violaceum* No. 968, *Escherichia coli* or *Burkholderia thailandensis*, may be genetically modified to express polypeptides having at least 80%, 85%, 90%, 95% or greater amino acid identity to one or more of DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), and DepN (SEQ ID NO: 27).

In another embodiment, one or more proteins of the FK228 biosynthetic pathway could be expressed in a bacterium in which an FK228 analog is synthesized, with the expectation that such bacteria would produce a unique FK228 analog. One such bacterium is *Burkholderia thailandensis* E264. As discussed in more detail below, *Burkholderia thailandensis* E264 makes a FK228 analog, designated as thailandepsin.

It is also envisioned that one or more of the sequences encoding DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27) could be modified or genetically manipulated to alter the specificity or activity of the encoded protein. For example, the coding sequences could be modified by site-directed mutagenesis or random mutagenesis to make specific substitutions of one or more amino acids. In another embodiment, sequences encoding specific modules or domains of one or more of the proteins of the FK228 biosynthetic pathway could be replaced with sequences encoding analogous modules or domains from other distinct, but related proteins, including, but not limited to, nonribosomal peptide synthetases (NRPS) or polyketide synthases (PKS), for example. Numerous NRPS and PKS are known in the art. It is envisioned that genetically engineered bacteria expressing such sequences can be used to develop bacterial strains capable of synthesizing FK228 analogs.

Provided herein is an FK228 analog, designated thailandepsin (Tdp), from *Burkholderia thailandensis* E264, which was elucidated as described in the Examples by its homology to the dep gene cluster (SEQ ID NO: 1). A tdp gene cluster (SEQ ID NO: 2) (Table 4, FIG. 5 and Appendix B) that encodes proteins involved in the biosynthesis of thailandepsin was identified in the genome of *Burkholderia thailandensis* E264 as described in the Examples. Although these sequences were published in GenBank as putative open reading frames, it was not known whether or not these sequences were actually expressed, nor was any function attributed to the gene products of the putative open reading frames. Nor was it appreciated that the genes constitute a cluster involved in the biosynthesis of an FK228 analog.

The coding sequences for proteins involved in biosynthesis of thailandepsin may be isolated from genomic *Burkholderia thailandensis* E264 DNA or mRNA and further modified or manipulated using standard methods. Accordingly, in yet another aspect, the invention includes an isolated polynucleotide encoding at least one polypeptide having at least 80%, 85%, 90%, 95% or greater amino acid identity to a protein encoded by tdpA (SEQ ID NO: 78), tdpB (SEQ ID NO: 76), tdpC1 (SEQ ID NO: 74), tdpC2 (SEQ ID NO: 70), tdpDE1 (SEQ ID NO: 72), tdpE2 (SEQ ID NO: 64), tdpF (SEQ ID NO: 68), tdpG (SEQ ID NO: 66), tdpH (SEQ ID NO: 62), tdpI (SEQ ID NO: 60), tdpJ (SEQ ID NO: 58), tdpL, or tdpN (SEQ ID NO: 80) operably connected to a promoter not natively associated with the coding sequence. Suitably, the polynucleotides encode TdpA (SEQ ID NO: 79), TdpB (SEQ ID NO: 77), TdpC1 (SEQ ID NO: 75), TdpC2 (SEQ ID NO: 71), TdpDE1 (SEQ ID NO: 73), TdpE2 (SEQ ID NO: 65), TdpF (SEQ ID NO: 69), TdpG (SEQ ID NO: 67), TdpH (SEQ ID NO: 63), TdpI (SEQ ID NO: 61), TdpJ (SEQ ID NO: 59), TdpL, or TdpN (SEQ ID NO: 81). The present invention also includes isolated polypeptides having at least 80%, 85%, 90%, 95%, or greater amino acid identity to TdpA (SEQ ID NO: 79), TdpB (SEQ ID NO: 77), TdpC1 (SEQ ID NO: 75), TdpC2 (SEQ ID NO: 71), TdpDE1 (SEQ ID NO: 73), TdpE2 (SEQ ID NO: 65), TdpF (SEQ ID NO: 69), TdpG (SEQ ID NO: 67), TdpH (SEQ ID NO: 63), TdpI (SEQ ID NO: 61), TdpJ (SEQ ID NO: 59), TdpL, or TdpN (SEQ ID NO: 81) and having the activity of TdpA (SEQ ID NO: 79), TdpB (SEQ ID NO: 77), TdpC1 (SEQ ID NO: 75), TdpC2 (SEQ ID NO: 71), TdpDE1 (SEQ ID NO: 73), TdpE2 (SEQ ID NO: 65), TdpF (SEQ ID NO: 69), TdpG (SEQ ID NO: 67), TdpH (SEQ ID NO: 63), TdpI (SEQ ID NO: 61), TdpJ (SEQ ID NO: 59), TdpL, or TdpN (SEQ ID NO: 81), respectively. The invention also includes vectors and recombinant or transgenic cells comprising one or more of the polynucleotides.

As discussed above for the FK228 biosynthetic pathway, the biosynthetic pathway of thailandepsin could be reconstituted in bacteria that do not natively possess the pathway, i.e., in bacteria other than *Burkholderia thailandensis* E264. The synthesis of thailandepsin in *Burkholderia thailandensis* E264 may be enhanced by introducing exogenous sequences expressing one or more polypeptides having least 80%, 85%, 90%, 95% or greater amino acid identity to a protein encoded by tdpA (SEQ ID NO: 78), tdpB (SEQ ID NO: 76), tdpC1 (SEQ ID NO: 74), tdpC2 (SEQ ID NO: 70), tdpDE1 (SEQ ID NO: 72), tdpE2 (SEQ ID NO: 64), tdpF (SEQ ID NO: 68), tdpG (SEQ ID NO: 66), tdpH (SEQ ID NO: 62), tdpI (SEQ ID NO: 60), tdpJ (SEQ ID NO: 58), tdpL, or tdpN (SEQ ID NO: 80). Additionally, recombinant *Burkholderia thailandensis* E264 could be made in the same manner as discussed above for *Chromobacterium violaceum* No. 968 to produce unique FK228 analogs.

The proposed synthesis scheme for thailandepsin is depicted in FIG. 6. Methods of producing an FK228 analog by growing *Burkholderia thailandensis* E264 are provided. *Burkholderia thailandensis* E264 may be grown in medium under conditions that allow for production of the FK228 analog and then the growth medium can be separated from the bacteria and the FK228 analog harvested. Those of skill in the art would appreciate that the FK228 analog may then be partially isolated using a variety of isolation techniques. The FK228 analog produced by this method may have unique properties. In the Examples, preliminary isolation and mass spectroscopy data indicate that three thailandepsins, designated thailandepsin A, thailandepsin B, and thailandepsin C, are made in *Burkholderia thailandensis* E264. (See FIG. 7 and FIG. 8). As will be readily appreciated by those of skill in the art, the thailandepsins share the same basic ring structure and backbone of FK228. The thailandepsins also share the disulfide bond found in FK228. Based on the mechanism of action of FK228 and the structural similarity of the thailandepsins and FK228, the thailandepsins are expected to act as HDAC inhibitors. The thailandepsins are distinct from FK228 at least at three locations.

As described more fully in the Examples, FK228 and thailandepsin are synthesized by sequential addition of simple moieties, such as amino acids, amino acid derivatives, or short carboxylic acids to form the backbone of the molecule. FK228 uses cysteine, valine, dehydro-threonine and malonyl coenzyme A (MCoA) as building blocks, while thailandepsins use cysteine, phenylalanine, alanine and/or glycine, and MCoA as building blocks. Based on these four identified species, the general structure of this family of molecules which are FK228 analogs may be depicted as follows:

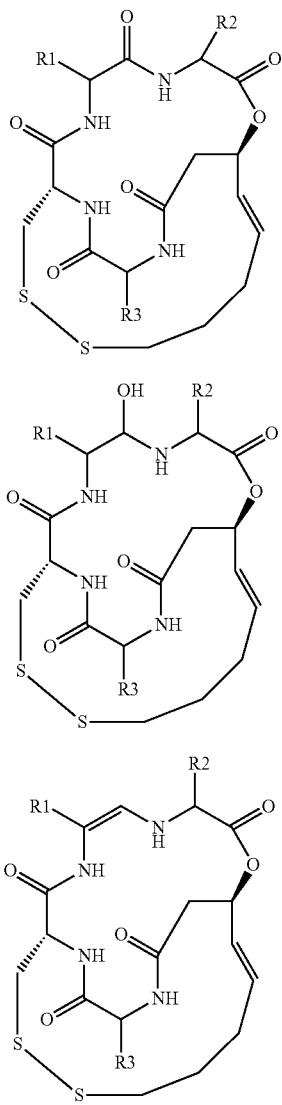

Formula (I)

Formula (II)

Formula (III)

wherein each of R1, R2 and R3 are an amino acid side chain or a derivative thereof. The amino acid side chains are well-known to those of skill in the art and include, e.g., alanine —CH$_3$; valine —CH(CH$_3$)$_2$; cysteine —CH$_2$SH; leucine —CH2CH(CH$_3$)$_2$; isoleucine —CH(CH$_3$)CH$_2$CH$_3$; and threonine —CH(OH)CH$_3$.

Figure 1:
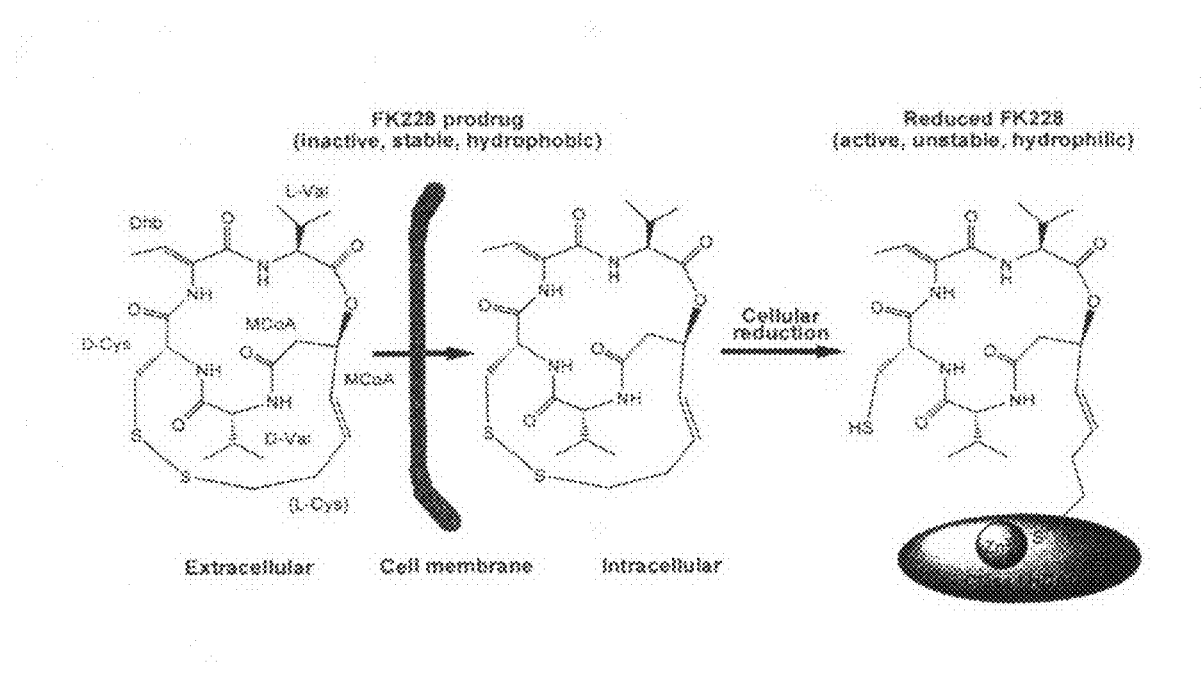
FIG. 1 depicts the structure of FK228 and its mode of action (modified from (Furumai, Matsuyama et al. 2002) with permission of the publisher).

Compounds of Formula (I), Formula (II) and Formula (III) in which each of R1, R2, and R3 are amino acid side chains are provided herein. The compounds may contain the disulfide bond as depicted in Formula (I), or the disulfide bond may be reduced as depicted in FIG. 1 to interact with HDACs in the cell. In addition, dehydration products of the molecules of Formula (I) and Formula (II) are provided. Dehydration may occur spontaneously as is the case with thailandepsin B and which results in formation of thailandepsin C, which is an analog belonging to formula III. Examples of compounds of formula (I) include, but are not limited to, a compound of formula (I), wherein R1 is —CHCH$_3$, R2 is —H, —CH$_3$, or —CH(CH$_3$)$_2$ and R3 is —CH$_3$ and a compound of formula (I), wherein R1 is —CHCH$_3$, R2 is —H or —CH$_3$ and R3 is —CH$_3$ or CH(CH$_3$)$_2$ and salts thereof.

Also encompassed are compounds of formula II or III, reduced forms of the compounds of formula II or III, dehydration products of the compounds of formula II or III, or salts thereof. Each of R1, R2, and R3 are an amino acid side chain or a derivative thereof. Examples of compounds of formula (II) include, but are not limited to, compounds of formula (II) wherein R1 is —CH$_2$-benzyl, wherein R2 is —H, —CH$_3$, or —CH(CH$_3$)$_2$ and wherein R3 is —CH$_3$ or —CH(CH$_3$)$_2$. Also included are thailandepsin A, thailandepsin B, thailandepsin C, formula (II) wherein R1 is —CH$_2$-benzyl, R2 is —CH(CH$_3$)$_2$, and R3 is —CH(CH$_3$)$_2$, formula (II) wherein R1 is —CH$_2$-benzyl, R2 is —CH(CH$_3$)$_2$, and R3 is —CH$_3$, formula (II) wherein R1 is —CH$_2$-benzyl, R2 is —H and R3 is —CH(CH$_3$)$_2$ and formula (II) wherein R1 is —CH$_2$-benzyl, R2 is —CH$_3$ and R3 is CH(CH$_3$)$_2$, formula (III) wherein R1 is —CH$_2$-benzyl, R2 is —CH(CH$_3$)$_2$, and R3 is —CH(CH$_3$)$_2$, formula (III) wherein R1 is —CH$_2$-benzyl, R2 is —CH(CH$_3$)$_2$, and R3 is —CH$_3$, formula (III) wherein R1 is —CH$_2$-benzyl, R2 is —H and R3 is —CH(CH$_3$)$_2$ and formula (III) wherein R1 is —CH$_2$-benzyl, R2 is —CH$_3$ and R3 is CH(CH$_3$)$_2$.

These FK228 and thailandepsin analogs may be made using routine microbial fermentation, bacterial genetics and molecular cloning procedures, such as those known to those of skill in the art, in combination with the disclosure of the dep and tdp gene clusters (SEQ ID NOS: 1 and 2) and structures of the resulting molecules.

The Examples also provide a gene inactivation protocol for Chromobacterium and Burkholderia, by which native sequences in the gene clusters encoding the synthetic apparatus for making FK228 and thailandepsin can be inactivated and non-native sequences can be inserted to produce novel FK228 and thailandepsin analogs. In the Examples, depD (SEQ ID NO: 34) was inactivated in C. violaceum No. 968 and TdpA (SEQ ID NO: 78) was inactivated in B. thailandensis E264. In both cases, inactivation of the gene resulted in bacteria that no longer made FK228 and thailandepsin, respectively. Similar methods could be used to inactivate any gene of interest, suitably any gene in the dep or tdp gene cluster (SEQ ID NOS: 1 and 2) may be inactivated using these methods.

Bacterial strains capable of synthesizing FK228 analogs may be developed from gene-inactivated mutants of Chromobacterium violaceum No. 968 or Burkholderia thailandensis E264 in which one or more genes involved in the biosynthesis of FK228 is inactivated by genetically manipulating the mutants to express a sequence encoding an analogous protein having a function similar to, but distinct from, that of the protein encoded by the native gene. The sequence encoding the analogous protein could be from a different bacterial genus, e.g., Burkholderia thailandensis E264, from a different species of Chromobacterium, from a different Chromobacterium violaceum isolate, from a different bacterial species, or it could be a chimeric sequence (e.g., a sequence encoding a protein having modules or domains ordinarily found on different proteins).

Provided herein are various methods for making FK228 and FK228 analogs. Notably, similar methods may be used to make thailandepsin and thailandepsin analogs as well. First, methods of making FK228 or an FK228 analog are provided. A recombinant cell comprising polynucleotides encoding proteins encoded by depA (SEQ ID NO: 28), depB (SEQ ID NO: 30), depC (SEQ ID NO: 32), depD (SEQ ID NO: 34), depE (SEQ ID NO: 36), depF (SEQ ID NO: 38), depG (SEQ ID NO: 40), depH (SEQ ID NO: 42), depI (SEQ ID NO: 44), depJ (SEQ ID NO: 46), depK (SEQ ID NO: 20), depL (SEQ ID NO: 22), depM (SEQ ID NO: 24), or depN (SEQ ID NO: 26) or a homolog thereof are grown by any suitable method. The polynucleotides are operably connected to a promoter, under conditions that allow synthesis of FK228 or an FK228 analog. Homologs of the proteins encoded by the dep gene cluster include, but are not limited to, proteins that share at least about 40%, 50%, 60%, 70% or more amino acid similarity and/or 25%, 35%, 45%, 55% or more amino acid identity and catalyzing analogous reactions. Homologs may share specific domains within the proteins. For example, candidate homologs for the dep gene cluster (SEQ ID NO: 1) may have NRPS, PKS or hybrid NRPS-PKS domains. The polynucleotides may be expressed in any suitable cell. Suitably, the cell is a bacterium of a genus selected from the group consisting of *Chromobacterium, Pseudomonas, Escherichia, Salmonella, Burkholderia, Bifidobacterium*, or *Clostridium*.

Alternatively, an FK228 analog can be made by introducing a polynucleotide into *Chromobacterium violaceum* No. 968 to produce a recombinant bacterium. The introduced polynucleotide encodes a polypeptide that is a homolog of at least one of DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepG (SEQ ID NO: 41), DepH (SEQ ID NO: 43), DepI (SEQ ID NO: 45), DepJ (SEQ ID NO: 47), DepK (SEQ ID NO: 21), DepL (SEQ ID NO: 23), DepM (SEQ ID NO: 25), or DepN (SEQ ID NO: 27), and the polynucleotide is operably connected to a promoter. The recombinant bacterium is then grown under conditions that allow expression of the polynucleotide and production of the FK228 analog. In one embodiment the polynucleotide encodes TdpE2 (SEQ ID NO: 65). Suitably, the native DepD (SEQ ID NO: 35) is inactivated in this embodiment. In another embodiment, the polynucleotide encodes TdpDE1 (SEQ ID NO: 73). Suitably the native DepE (SEQ ID NO: 37) is inactivated in the recombinant bacterium of this embodiment. Similar methods may be used to make a thailandepsin analog. In one embodiment, the polynucleotide introduced into *B. thailandensis* encodes DepD (SEQ ID NO: 35). Suitably tdpE2 (SEQ ID NO: 65) is inactivated in the recombinant bacterium in this embodiment. In another embodiment, the polynucleotide introduced into *B. thailandensis* encodes DepE (SEQ ID NO: 37). Suitably tdpDE1 (SEQ ID NO: 73) is inactivated in the recombinant bacterium in this embodiment.

In yet another embodiment, methods of producing FK228 or an FK228 analog in *Chromobacterium violaceum* No. 968 are provided. Analogs may be made by manipulating at least one of the polynucleotides in the dep gene cluster (SEQ ID NO: 1) to produce a mutated polynucleotide and then introducing the mutated polynucleotide into *Chromobacterium violaceum* No. 968. The polynucleotides are operably connected to a promoter such that they are expressed in the recombinant bacteria. Similar methods may be used to make thailandepsin analogs in *B. thailandensis* E264.

Suitably the FK228 and thailandepsin analogs have histone deacetylase inhibitor activity. Assays for histone deacetylase inhibition are known to those of skill in the art and may be used to assess whether the analogs are active. The FK228 and thailandepsin analogs may be used in pharmaceutical compositions and administered to subjects to treat disease. Pharmaceutically acceptable carriers are well known to those of skill in the art.

The FK228 analogs described herein may be used to treat diseases associated with increased histone deacetylation by administering an effective amount of an FK228 analog to a subject with such a disease. Diseases include, but are not limited to, inflammatory disorders, diabetes, diabetic complication, homozygous thalassemia, fibrosis, cirrhosis, tumor, acute myeloid leukemia (AML), chronic lymphocytic leukemia (CLL), neurodegenerative disease, cognitive disorder, and autoimmune disease. Treatment of a disease includes but is not limited to, prophylaxis of symptoms, reduction in disease severity, or reduction in disease length as compared to an untreated subject.

Administration of an effective amount of a FK228 analog to a subject may be carried out by any means known in the art including, but not limited to intraperitoneal, intravenous, intramuscular, subcutaneous, or transcutaneous injection or oral, nasopharyngeal or transmucosal absorption. Determination of a preferred pharmaceutical formulation and a therapeutically effective dose regimen for a given application is within the skill of the art taking into consideration, for example, the condition and weight of the patient, the extent of desired treatment and the tolerance of the patient for the treatment.

Methods of reducing histone deacetylase-mediated inhibition of gene expression in a cell are also provided. These methods include contacting the cell with an effective amount of a composition comprising an FK228 analog compound. The FK228 analog is capable of inhibiting HDACs. The HDACs are known to inhibit gene expression, thus inhibition of HDACs may result in increased expression of genes. As used herein gene encompasses polynucleotides encoding for polypeptides natively associated with the cell as well as polynucleotides encoding non-native polypeptides. Effects of contacting a cell with a FK228 analog may be evaluated by comparing expression of a polynucleotide in cells treated with the FK228 analog to expression in untreated cells. Expression of a polynucleotide may be assessed by any means known to those of skill in the art, including but not limited to, rtPCR, Northern analysis, and Western analysis.

The yield of FK228 production from its native bacterial strain, *C. violaceum* No. 968, is low (Ueda, Nakajima et al. 1994). Production of FK228 may be improved using the methods of the invention. The nucleic acid sequence of a regulatory gene, depL (SEQ ID NO: 22), is provided herein. The regulatory genes depL (SEQ ID NO: 22) and its *B. thailandensis* homolog, tdpL, regulate the expression of the entire dep or tdp gene cluster (SEQ ID NOS: 1-2). Thus, genetic manipulation of these genes may improve production of FK228 and thailandepsin. The expression level of depL (SEQ ID NO: 22) can be increased by increasing the copy number of the gene by, for example, supplementing the polynucleotide encoding DepL (SEQ ID NO: 23) on a multi-copy plasmid or integrating multiple copies of depL (SEQ ID NO: 22) into the chromosome, and/or by cloning the intact gene into an expression vector with a strong promoter and subsequently introducing the construct into the wild-type strain or any genetically engineered strains of *C. violaceum* No. 968. The expression level of depL (SEQ ID NO: 22) can also be decreased by design and expression of an anti-sense of depL (SEQ ID NO: 22), and/or by deleting various amounts of the depL (SEQ ID NO: 22) gene upstream regulatory elements in the wild-type strain or any genetically altered strains of *C. violaceum* No. 968. Alternatively, the depL (SEQ ID NO: 22) expression level could be abolished by targeted gene inactivation as described for depD (SEQ ID NO: 34) in the Examples. The sequence encoding DepL (SEQ ID NO: 23) can be further mutated to encode DepL variants with altered activity and/or specificity. FK228 production can be assessed by conventional natural product purification and identification procedures.

Disulfide bonds that link two nonadjacent (in most cases) cysteines often exist in proteins and peptides, and their derived products, such as lantibiotics, toxins, venoms and hormones, to maintain proper folding configuration. Enzymes that are capable of catalyzing protein/peptide disulfide bond formation are members of a large collection of thiol-disulfide oxidoreductases found in all living cells. Many of these enzymes belong to the thioredoxin superfamily, which is defined by an active site containing a CXXC motif (cysteines separated by two amino acids) and by a thioredoxin fold seen in the three-dimensional structure (Kadokura, Katzen et al. 2003). The best studied catalyst of disulfide bond formation is the DsbA and its associated proteins (DsbB, DsbC, and DsbD) in *E. coli*.

Disulfide bonds are also, however rarely, found in small molecule natural products (e.g. FK228 and thailandepsins, psammaplins (Pina, Gautschi et al. 2003), triostins (precursors of echinomycins), thiocoraline, BE-22179 and SW-163C (Lombo, Velasco et al. 2006; Watanabe, Hotta et al. 2006; Dawson, Malkinson et al. 2007)). In the triostin/echinomycin biosynthetic gene cluster, a gene, ecm17, encodes an FAD-dependent pyridine nucleotide-disulphide oxidoreductase (S1_Ecm17; accession no. BAE98166) that catalyzes a disulfide bond formation between two cysteine residues (Watanabe, Hotta et al. 2006). Despite a high degree of structural similarity between triostins and thiocoraline, surprisingly, the thiocaroline biosynthetic gene cluster does not contain an apparent gene encoding a disulfide bond formation enzyme (Lombo, Velasco et al. 2006).

Figure 9:
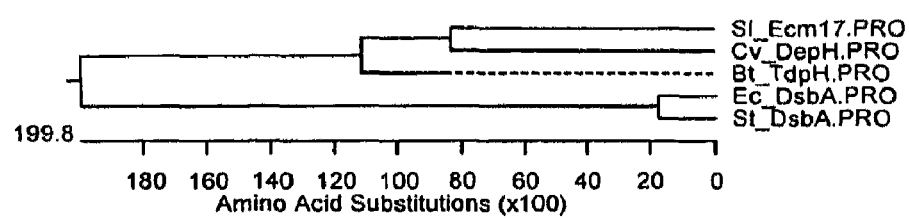
FIG. 9a depicts the results of a phylogenetic analysis of five disulfide bond formation enzymes, which clearly categorizes Cv_DepH (SEQ ID NO: 43), Bt_TdpH (SEQ ID NO: 63) and Sl_Ecm17 into a new group, distinct from the DsbA group of enzymes.
FIG. 9b is a sequence alignment of the region encompassing the active site containing a CXXC motif (bold type) among all five disulfide bond formation enzymes.

In the FK228 biosynthetic gene cluster, a particular gene, depH (SEQ ID NO: 42), was identified that encodes an FAD-dependent pyridine nucleotide-disulphide oxidoreductase (Cheng, Yang et al. 2007). In the thailandepsin biosynthetic gene cluster, a particular gene, tdpH (SEQ ID NO: 62), was identified that encodes an FAD-dependent pyridine nucleotide-disulphide oxidoreductase. See the Examples. The deduced protein sequences of DepH (SEQ ID NO: 43) (GenBank accession no. ABP57752) and TdpH (SEQ ID NO: 63) (GenBank accession no. ABC38333) have a 72% identity/85% similarity to each other. Either DepH (SEQ ID NO: 43) or TdpH (SEQ ID NO: 63) sequence has a 32% identity/46% similarity to the deduced Ecm17 protein sequence of ecm17 gene in the triostin/echinolycin biosynthetic gene cluster. DepH (SEQ ID NO: 43), TdpH (SEQ ID NO: 63) or Ecm17 sequences have no significant similarity to DsbA of *E. coli*, except sharing an active site containing a CXXC motif (FIG. 9). Thus, DepH (SEQ ID NO: 43), TdpH (SEQ ID NO: 63) and Ecm17 appear to constitute a new group of disulfide bond formation enzymes that are distinct from the DsbA enzymes. DepH (SEQ ID NO: 43), TdpH (SEQ ID NO: 63) and Ecm17 are the only known or proposed enzymes involved in the disulfide bond formation in natural product biosynthesis; therefore, their genes can be exploited biosynthetically for the formation of disulfide bonds in new drug molecules. Similarly, the DepH (SEQ ID NO: 43), TdpH (SEQ ID NO: 63) and Ecm17 proteins can be also exploited as catalysts for in vitro conversion of chemical precursors containing two free thiols into products with a disulfide bond.

FIG. 9 depicts the relationship of several proteins capable of forming disulfide bonds. Ec_DsbA.PRO is the protein sequence of DsbA of *Escherichia coli* K12 (GenBank accession no. AAB02995) and is known to be involved in protein/peptide disulfide bond formation. St_DsbA.PRO shows the protein sequence of DsbA of *Salmonella typhimurium* LT2 (GenBank accession no. NP_462877), which is also known to be involved in protein/peptide disulfide bond formation. Cv_DepH depicts the protein sequence of DepH (SEQ ID NO: 43) of *Chromobacteriumm violaceum* No. 968 (GenBank accession no. ABP57752), which is known to be involved in the disulfide bond formation in FK228. Bt_TdpH depicts the protein sequence of TdpH (SEQ ID NO: 63) of *Burkholderia thailandensis* E264 (GenBank accession no. ABC38333), which is proposed to be involved in the disulfide bond formation in thailandepsins. Finally, S1_Ecm17 depicts the protein sequence of Ecm17 of *Streptomyces lasaliensis* (GenBank accession no. BAE98166), which is involved in the disulfide bond formation in triostins.

In yet another embodiment, methods of catalyzing a disulfide bond in a chemical comprising at least two free thiol or sulfhydryl groups are provided. The chemical is contacted with a polypeptide having at least 80% amino acid identity to a protein encoded by Ecm17, DepH (SEQ ID NO: 43) or TdpH (SEQ ID NO: 63). The Ecm17, DepH (SEQ ID NO: 43) or TdpH (SEQ ID NO: 63) polypeptide catalyzes formation of a disulfide bond between the two free thiols. Suitably the chemical comprises a macrolide ring structure. The chemical may be contacted by the polypeptide using any means known to those of skill in the art. In one embodiment, the chemical is contacted by the polypeptide by introducing a polynucleotide encoding the polypeptide into a cell in which the chemical is synthesized.

A generic formula for the substrate for Ecm17, DepH (SEQ ID NO: 43) or TdpH (SEQ ID NO: 63) is as follows:

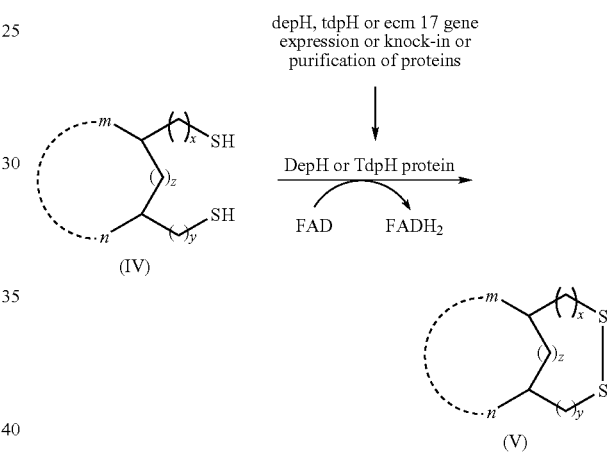

wherein FAD is a cofactor required by the FAD-dependent pyridine nucleotide-disulphide oxidoreductase (DepH (SEQ ID NO: 43), TdpH (SEQ ID NO: 63), or Ecm17) and $FADH_2$ is the reduced form of FAD. X and y represent any number of C—C units in any format. Z represents any number of any type bonds (C—C, C—N, or C—O) in any format. M and n represent any chemical moieties, but preferred ones that form a macrolide ring structure.

Sequences encoding a polypeptide having at least 80% amino acid identity to DepH (SEQ ID NO: 43), TdpH (SEQ ID NO: 63) or Ecm17 can be used to form disulfide bonds in drug molecules by (1) cloning the sequence into a suitable expression vector to make an expression construct; (2) introducing the construct into a microorganism that produces a precursor or multiple precursors, according to formula (IV) to produce the desired enzyme, which in turn catalyzes the conversion of the precursor into a disulfide bond product according to formula (V).

Alternatively, sequences encoding a polypeptide having at least 80% amino acid identity to DepH (SEQ ID NO: 43), TdpH (SEQ ID NO: 63) or Ecm17 can be used to form disulfide bonds in drug molecules by (1) cloning the sequence into a suitable integrative vector to make an integrative construct; (2) introducing the construct into a microorganism that produces a precursor or multiple precursors, according to formula (IV); and (3) selecting strains with the sequence integrated into the bacterial chromosome, such that the sequence is expressed and produces an enzyme capable of catalyzing the conversion of the precursor into a disulfide bond product according to formula (V).

DepH (SEQ ID NO: 43), TdpH (SEQ ID NO: 63), or Ecm17 protein can be used to catalyze the formation of disulfide bonds in drug molecules in vitro. The protein can be expressed in and purified from a heterologous host, including but not limited to, *E. coli, Streptomyces lividans*, or yeasts. The purified enzyme is contacted with a precursor according to formula (IV) under suitable conditions of temperature, pressure, pH, cofactors, etc., to catalyze the conversion of the precursor to a disulfide bond-containing product according to formula (V).

The following examples are meant to be illustrative only and are not meant to be limiting upon the invention claimed.

EXAMPLES

Materials and Methods

Bacterial strains, culture conditions, and plasmids. The bacterial strains and plasmids used in this study are listed in Table 1. The FK228-producing strain, *C. violaceum* No. 968, was cultured in nutrient broth (1% Difco nutrient broth and 1% glucose) at 30° C. for genomic DNA preparation and in fermentation medium (nutrient broth supplemented with 5% Diaion HP-20 resin [Supelco, Pennsylvania]) at 30° C. for FK228 production. The vectors pEX18Tc and pPS858, originally developed for *Pseudomonas aeruginosa* genetics (Hoang, Karkhoff-Schweizer et al. 1998), were adopted and applied successfully in *C. violaceum*.

TABLE 1

Bacterial strains and plasmids used in this study

| Strain(s) or plasmid(s) | Description | Source or reference(s) |
|---|---|---|
| *Chromobacterium violaceum* | | |
| No. 968 (=FERM BP-1968) | Wild type, FK228 producing, $Ap^r$ $Thio^{ra}$ | $IPOD^b$ |
| Cv56a/b/c | Serial mutants with an internal part of pP3-B6 DNA replaced by the FRT cassette ($Gm^r$ $GFP^+$) from pPS858, FK228 producing | This study |
| Cv57a/b/c | Serial mutants with an internal part of pP4-B4 DNA (on depD gene) replaced by the FRT cassette ($Gm^r$ $GFP^+$) from pPS858, non-FK228 producing | This study |
| Cv58a/b/c | Serial mutants with an internal part of pP4-G7 DNA (on depD gene) replaced by the FRT cassette ($Gm^r$ $GFP^+$) from pPS858, non-FK228 producing | This study |
| *Escherichia coli* | | |
| DH5α | General cloning host | (Sambrook and Russell 2000) |
| XL1-Blue MR | Host strain for cosmid library construction | Stratagene |
| S17-1 | Host strain for interspecies conjugation | (Simon, Priefer et al. 1983) |
| ET12567(pUZ8002) | Alternative host strain (methylation-deficient) for conjugation | (MacNeil, Gewain et al. 1992; Kieser, Bibb et al. 2000) |
| MT670(pRK600) | Alternative host strain for conjugation | (Finan, Kunkel et al. 1986) |
| Plasmids | | |
| pGEM-3Zf | $Ap^r$, general cloning vector | Promega |
| pGEM-T Easy | $Ap^r$, general cloning vector | Promega |
| pP3-A6 | 2.8-kb random genomic DNA of *C. violaceum* cloned into pGEM-T Easy, sequenced | This study |
| pP4-B4 | 3.6-kb random genomic DNA of *C. violaceum* cloned into pGEM-T Easy, sequenced | This study |
| pP4-G7 | 2.6-kb random genomic DNA of *C. violaceum* cloned into pGEM-T Easy, sequenced | This study |
| pPS858 | $Ap^r$ $Gm^r$ $GFP^+$, source of the FRT cassette | (Hoang, Karkhoff-Schweizer et al. 1998) |
| pYC03-56a | $Ap^r$ $Gm^r$ $GFP^+$, replacement of an internal 1.8-kp EcoRV fragment on pP3-A6 by a 1.8-kb SmaI fragment (containing the FRT cassette) from pPS858 | This study |
| pYC03-57a | $Ap^r$ $Gm^r$ $GFP^+$, replacement of an internal 1.1-kb BglII/NruI fragment on pP4-B4 (blunt ended) by a 1.8-kb SmaI fragment (containing the FRT cassette) from pPS858 | This study |
| pYC03-58a | $Ap^r$ $Gm^r$ $GFP^+$, replacement of two adjacent internal NruI fragments (456 bp and 489 bp) on pP4-G7 (blunt-ended) by a 1.8-kb SmaI fragment (containing the FRT cassette) from pPS858 | This study |
| pEX18Tc | $Tc^r$ $oriT^+$ $sacB^+$, gene replacement vector, conjugative | (Hoang, Karkhoff-Schweizer et al. 1998) |
| pYC03-56b | Conjugative construct with a 2.8-kb NotI fragment (blunt ended, containing the FRT cassette and flanking DNAs) from pYC03-56a ligated into the SmaI site of pEX18Tc | This study |
| pYC03-57b | Conjugative construct with a 4.3-kb NotI fragment (blunt ended, containing the FRT cassette and flanking DNAs) from pYC03-57a ligated into the SmaI site of pEX18Tc | This study |
| pYC03-58b | Conjugative construct with a 3.7-kb PstI/SphI fragment (blunt ended, containing the FRT cassette and flanking DNAs) from pYC03-58a ligated into the SmaI site of pEX18Tc | This study |

TABLE 1-continued

Bacterial strains and plasmids used in this study

| Strain(s) or plasmid(s) | Description | Source or reference(s) |
| --- | --- | --- |
| SuperCos 1 | Ap[r] Kan[r], cosmid vector | Stratagene |
| Cosmid 18 | Cosmid clone containing the FK228 biosynthetic gene cluster (dep) and flanking DNAs, shotgun sequenced | This study |
| Cosmid 2 | Cosmid clone containing a partial dep gene cluster | This study |
| pCos2S1 to pCos2S5 | BamHI fragments (4.0, 0.8, 6.2, 4.5, and 7.7 kb, respectively) of cosmid 2 inserted into the same site of pGEM-3Zf, sequenced by the primer walking method | This study |

[a]Thio[r], thiostrepton resistance.
[b]IPOD, International Patent Organism Depositary, Tsukuba, Japan.

DNA manipulations, genome library construction, and DNA sequencing. General DNA manipulations, including plasmid preparation, restriction enzyme digestion, agarose gel electrophoresis, subcloning, and bacterial transformation, were done according to standard protocols (Sambrook and Russell 2000) or manufacturer's instructions (New England BioLabs; QIAGEN). Genomic DNA of a C. violaceum wild-type or mutant strain was prepared from an overnight culture with a Genomic-tip 500/G kit (QIAGEN) or with an Ultra-Clean Microbial DNA Isolation kit (MO BIO Labs).

For construction of a genome sampling library (Zazopoulos, Huang et al. 2003), high-molecular-weight C. violaceum genomic DNA was mechanically sheared with a nebulization device (Invitrogen). DNA molecules that were 2 to 4 kb long were recovered from an agarose gel and ends repaired with T4 DNA polymerase and Klenow enzyme in the presence of deoxynucleotide triphosphates (dNTPs; 1 mM each). The ends of resultant DNA molecules were adenylated using Taq DNA polymerase with dATP, ligated to the pGEM-T Easy vector, and transformed into Escherichia coli DH5α cells. Four 96-well plates of clones were subjected to template DNA preparation by PCR amplification and purification with a PerfectPrep PCR Cleanup 96 kit (Eppendorf), and end sequencing with BigDye chemistry and SP6 as primer was performed on an ABI 3730 automated DNA sequencer (Applied Biosystems) at the University of Wisconsin-Madison Biotechnology Center. DNA oligonucleotides were synthesized by Operon Biotechnologies, Inc., and DNA sequencing by primer walking was performed by standard procedures (Sambrook and Russell 2000).

A cosmid library was constructed in the SuperCos 1 vector using previously described procedures (Cheng 2006). Southern blotting, labeling of DNA as a probe, hybridization, and detection were performed according to manufacturer's protocols (Roche). Shotgun sequencing of cosmid 18 and contig assembling were performed by a service company (ACGT Inc.). Local sequence analysis was performed with the Lasergene program package (DNASTAR, Inc.), and by a homology search against the GenBank database using the BLAST algorithms (Altschul, Gish et al. 1990). The domain organization of biosynthetic enzymes was analyzed as described by Ansari et al. (Ansari, Yadav et al. 2004), with manual intervention.

General strategy for the construction of targeted gene-inactivated mutants of C. violaceum No. 968. To mutate a candidate gene by a gene replacement strategy, an internal part of the DNA of a genomic DNA clone (Ap[r], ampicillin resistant) was replaced by a 1.8-kb FRT cassette (Gm[r], gentamycin resistant) from pPS858 to make an intermediate construct (Ap[r] Gm[r]). The FRT cassette, along with two flanking genomic DNAs for homologous DNA recombination, was excised and subcloned into pEX18Tc to make a final conjugation construct (Gm[r] and tetracycline resistant—Tc[r]).

The conjugation construct was introduced into E. coli S17-1 cells and subsequently transferred into C. violaceum cells by conjugation as follows. Two bacterial strains were grown in LB media supplemented with appropriate antibiotics (10 µg/ml Gm and 10 µg/ml Tc for E. coli S17-1 [a conjugation construct] and 200 µg/ml Ap for C. violaceum, which is naturally resistant to Ap) at 37 or 30° C. with shaking until late mid-log phase (6 to 8 h). Cells from 1 ml of each culture were collected by centrifugation at 4,000×g for 15 min at 4° C., and the cell pellets were washed once with 1 ml LB medium. Cells were collected again by centrifugation and resuspended in 100 µl LB medium. Cell suspensions of two bacterial strains were pooled and spread evenly on a wet 0.45-µm nitrocellulose membrane (Whatman) on LB agar supplemented with 10 mM $MgSO_4$. After the plate had been incubated at 30° C. for 12 to 16 h, the membrane seeded with bacteria was used to print several LB agar plates containing 200 µg/ml Ap, 50 µg/ml Gm and 5% sucrose to select for exconjugants.

FK228 production and detection by LC-MS. Wild-type and mutant strains of C. violaceum were grown in 25 ml of fermentation medium at 30° C. for 3 days under constant agitation (200 rpm). Cells and resins were then collected together by centrifugation at 4,000×g for 20 min at the ambient temperature and lyophilized to dryness. A crude FK228 preparation was obtained by eluting the dried cell debris and resins with 10 ml ethyl acetate. Twenty microliters of this preparation was injected into an Agilent 1100 Series LC/MSD Trap mass spectrometer (MS) (Agilent) for detection of the positive ion signals of FK228. The liquid chromatography (LC) program included a linear gradient from buffer A (20% methanol with 0.1% formic acid) to buffer B (80% methanol with 0.1% formic acid) in 15 min and a constant elution in buffer B for 5 min, followed by a linear return to buffer A in 5 min. Samples were fractionated by using a Zorbax Eclipse XDB-$C_{18}$ column (2.1 by 110 mm; Agilent) with a flow rate of 0.25 ml/min.

Nucleotide sequence accession numbers. The nucleotide sequences of the inserts in pP3-B6, pP4-B4, pP4-G7, and cosmid 18 have been deposited in the GenBank database under accession numbers EF015612, EF015613, EF015614, and EF210776, respectively. The nucleotide sequence of the dep gene cluster is included herein as SEQ ID NO:1. The putative amino acid sequences are also in the appended sequence listing.

Results and Discussion

Identification of candidate natural product biosynthetic genes in C. violaceum No. 968. The hybrid NRP-PK-NRP nature of FK228 (FIG. 1) suggests that FK228 is likely biosynthesized by a hybrid NRPS-PKS-NRPS assembly line, probably with an additional enzymatic activity for the formation of an intramolecular disulfide bond. The biosynthesis of NRPs, PKs, and hybrid NRP-PK or PK-NRP natural products via successive condensation of simple building blocks, such as amino acids, amino acid derivatives, and short carboxylic acids, catalyzed by NRPSs, PKSs, and hybrid NRPS-PKS or PKS-NRPS systems, respectively, has been studied.

For ester bond formation in depsipeptide natural products, the involvement of a discrete D-hydroxyisovalerate dehydrogenase in enniatin biosynthesis by *Fusarium sambucinum* (Lee, Gorisch et al. 1992), or a novel NRPS module containing an adenylation (A) domain to activate an α-keto acid and an embedded α-ketoreductase (KR) to reduce the tethered substrate into α-hydroxyacyl intermediate (and presumably a downstream condensation [C] domain acting as chiral ester synthase rather than an amide synthase) in cereulide and valinomycin biosynthesis in actinomycetes (Magarvey, Ehling-Schulz et al. 2006), has been experimentally established. However, whether intramolecular disulfide bond formation in natural products (such as FK228) is an enzymatic reaction or a spontaneous chemical oxidation is unknown. Therefore, our search for candidate FK228 biosynthetic genes focused initially on those encoding an obvious NRPS, PKS, or, in particular, hybrid NRPS-PKS or PKS-NRPS system.

Among 360 valid sequence tags obtained from sequencing of the genome sampling library of *C. violaceum* (See Materials and Methods), three distinctive sequence tags, P3-A6-SP6, P4-B4-SP6, and P4-G7-SP6, were identified to be parts of genes encoding PKS, NRPS, and hybrid PKS-NRPS system, respectively (Table 2). Genes that contain those three tags were considered as candidate natural product biosynthetic genes, possibly involved in FK228 biosynthesis. Further primer walking sequencing revealed the complete sequences of the corresponding inserts in pP3-A6, pP4-B4, and pP4-G7.

The insert in pP3-A6 contains a 2,826-bp DNA that includes a partial PKS gene (not named) and its translated amino acid sequence has homology to the β-ketoacyl synthase (KS) and acyltransferase (AT) domains of type I PKSs (Shen 2003). Three signature motifs (QTRTAQ (SEQ ID NO. 3), GHSYG (SEQ ID NO. 4), and AAFH (SEQ ID NO. 5)) were identified within the AT domain, and these motifs are similar to the motifs of ATs using MCoA as a substrate (Reeves, Murli et al. 2001).

The insert in pP4-B4 contains a 3,612-bp DNA that includes a partial gene (designated depD (SEQ ID NO: 34)) (Table 3 and FIG. 2A), and its translated amino acid sequence has homology to the A, peptidyl carrier protein (PCP), and epimerase (E) domains of type A NRPSs (Mootz, Schwarzer et al. 2002). The "NRPS substrate specificity codes" of the A domain was identified as DLFEMSLIWK (SEQ ID NO. 6), and this A domain is predicted to activate L-Cys, according to Ansari et al. (Stachelhaus, Mootz et al. 1999; Challis, Ravel et al. 2000; Ansari, Yadav et al. 2004).

The insert in pP4-G7 contains a 2,599-bp DNA that includes two partial genes (designated depC (SEQ ID NO: 32) and depD (SEQ ID NO: 34)) (Table 3 and FIG. 2A), and their translated amino acid sequences have homology to the KR and acyl carrier protein (ACP) domains of PKSs, followed by the C and A domains of NRPSs, indicating a hybrid PKS-NRPS system (Du, Cheng et al. 2003). The A domain is incomplete; therefore, the "NRPS substrate specificity codes" cannot be extracted for prediction of substrate specificity. Inserts in pP4-B4 and pP4-G7 cover different parts of the same depD (SEQ ID NO: 34) gene.

TABLE 2

Properties of three sequence tags and their associated candidate (partial) genes

| Sequence tag | Recombinant plasmid | size (bp) | Associated gene(s)[a] | Protein homolog(s) (accession no.) | Domain organization[b] | Protein classification | Signature motif(s) or substarte specificity codes |
|---|---|---|---|---|---|---|---|
| P3-A6-SP6 | pP3-A6 | 2,826 | NN[c] | JamL (AAS98783) | KS-AT[i] | Type I PKS | QTRTAQ, GHSYG, and AAFH in AT domain |
| P4-B4-SP6 | pP4-B4 | 3,612 | depD | BmyB (CAE11249) | C[i]-A-PCP-E | Type A NRPS | DLFEMSLIWK in A domain |
| P4-07-SP6 | pP4-G7 - | 2,599 | depC, depD | Ampt1 (AAK73501), NosC (AAF17280) | KR[i]-ACP, C-A[i] | FRS, NRPS | NM |

| Predicted substrate specificity | Necesssary for FK228 biosynthesis |
|---|---|
| MCoA | No |
| L-Cys | Yes |
| NA | Yes |

[a]See FIG. 2.
[b]A superscript I indicates incomplete. KS, β-ketoacyl synthase; E, epimerase.
[c]NN, not named.
[d]NA, not available.

TABLE 3

Deduced functions of open reading frames and genes in the dep gene cluster and flanking regions

| Open reading frame or gene | Protein size (amino acids) | Protein homolog | Accession no. | % Identity/ % similarity | Origin | Proposed function[a] |
|---|---|---|---|---|---|---|
| orf1[b] (SEQ ID NO: 14) | 150[c] | CV_3386 | AAQ61050 | 87/93 | *C. violaceum* ATCC 12472 | 16S rRNA pseudouridine synthase |
| orf2 (SEQ ID NO: 16) | 163 | CV_3385 | AAQ61049 | 66/76 | *C. violaceum* ATCC 12472 | MutT/nudix family phosphohydrolase |
| orf3 (SEQ ID NO: 18) | 190 | CV_3384 | AAQ61048 | 88/94 | *C. violaceum* ATCC 12472 | Transcription elongation factor GreB |
| depK (SEQ ID NO: 20) | 85 | CCO_1235 | EAL57087 | 36/52 | *Campylobacter coli* RM2228 | Conserved hypothetical protein, function unknown |
| depL (SEQ ID NO: 22) | 155 | CV_3383 | AAQ61047 | 68/78 | *C. violaceum* ATCC 12472 | Helix-turn-helix transcriptional regulator, MarR family |
| depM (SEQ ID NO: 24) | 389 | PFL_4362 | AAY93617 | 59/73 | *Pseudomonas fluorescens* Pf-5 | Aminotransferase, class I and II family protein |
| depN (SEQ ID NO: 26) | 65 | — | — | — | — | PCP[a] |
| depA (SEQ ID NO: 28) | 1697 | SafB | AAC44128 | 31/45 | *Myxococcus xanthus* strain Mx x48 | NRPS: AL$^i$-C$^a$-A$_{Cys}$-PCP |
| depB (SEQ ID NO: 30) | 1553 | CurG | AAT70102 | 45/61 | *Lyngbya majuscula* | PKS: KS-AT$^a$-DH$^a$-KR$^i$-ACP |
| depC (SEQ ID NO: 32) | 1183 | CrpB | ABM21570 | 44/64 | *Nostoc* sp. ATCC 53789 | PKS: KS-DH$^a$-KR$^i$-ACP |
| depD (SEQ ID NO: 34) | 3057 | PvdI | AAX16361 | 36/51 | *Pseudomonas aeruginosa* | NRPS: C-A$_{Val}$-PCP-E-C-A$_{Cys}$-PCP-E |
| depE (SEQ ID NO: 36) | 1892 | McyB | BAA83993 | 35/52 | *Microcystis aeruginosa* | NRPS: C-A$_{Dbb}$-PCP-C-PCP-TE |
| depF (SEQ ID NO: 38) | 390 | PP_2437 | AAN68049 | 38/56 | *Pseudomonas putida* KT2440 | FadE2-like acyl-CoA dehydrogenase |
| depG (SEQ ID NO: 40) | 321 | PSPTO_2724 | AAO56225 | 32/53 | *Pseudomonas syringae* pv. tomato DC3000 | Phosphotransferase |
| depH (SEQ ID NO: 42) | 319 | PA4170 | AAG07557 | 56/70 | *Pseudomonas aeruginosa* PAO1 | FAD-dependent pyridine nucleotide-disulphide oxidoreductase |
| depI (SEQ ID NO: 44) | 304 | RRSL_03772 | EAP73858 | 54/65 | *Ralstonia solanacearum* UW551 | Putative esterase/Lipase |
| depJ (SEQ ID NO: 46) | 254 | LnmN | AAN85527 | 43/58 | *Streptomyces atroolivaceus* S-140 | Type II thioesterase |
| orf18 (SEQ ID NO: 48) | 312 | CV_3378 | AAQ60142 | 87/93 | *C. violaceum* ATCC 12472 | Hydrogen peroxide-inducible genes activator OxyR |
| orf19 (SEQ ID NO: 50) | 85 | CV_3377 | AAQ60141 | 92/98 | *C. violaceum* ATCC 12472 | Cell division topological specificity factor MinE |
| orf20 (SEQ ID NO: 52) | 270 | CV_3376 | AAQ61040 | 92/98 | *C. violaceum* ATCC 12472 | Septum site-determining protein MinD |
| orf21[b] (SEQ ID NO: 54) | 107[c] | CV_3375 | AAQ61039 | 93/97 | *C. violaceum* ATCC 12472 | Septum formation inhibitor MinC |

[a]Subscripts indicate the substrate specificities of enzymes. Superscripts indicate inactive (i) or nonfunctional (n). Dhb, 2-3-dehydro-2-aminobutanic acid.
[b]Incomplete.
[c]Truncated.

Adaptation of a *Pseudomonas aeruginosa* genetic system in *C. violaceum* No. 968 to create targeted gene-inactivated mutant strains. To test whether the identified candidate genes are necessary for FK228 biosynthesis, we inactivated the individual genes (except depC (SEQ ID NO: 32), which has only a very short segment on the insert of pP4-G7) in *C. violaceum* No. 968. *C. violaceum* strains belong to the gram-negative β-proteobacterium. Although isolates of *C. viola-* ceum produce many products with biotechnological and pharmaceutical utility, and the genome of a type strain, *C. violaceum* ATCC 12472, has been sequenced (Consortium 2003), a genetic system for targeted gene inactivation in *C. violaceum* has not been reported. Here, a broad-host-range Flp-FRT recombination system originally developed for *P. aeruginosa* genetics (Hoang, Karkhoff-Schweizer et al. 1998) was adopted and successfully applied to *C. violaceum* No. 968.

Figure 3:
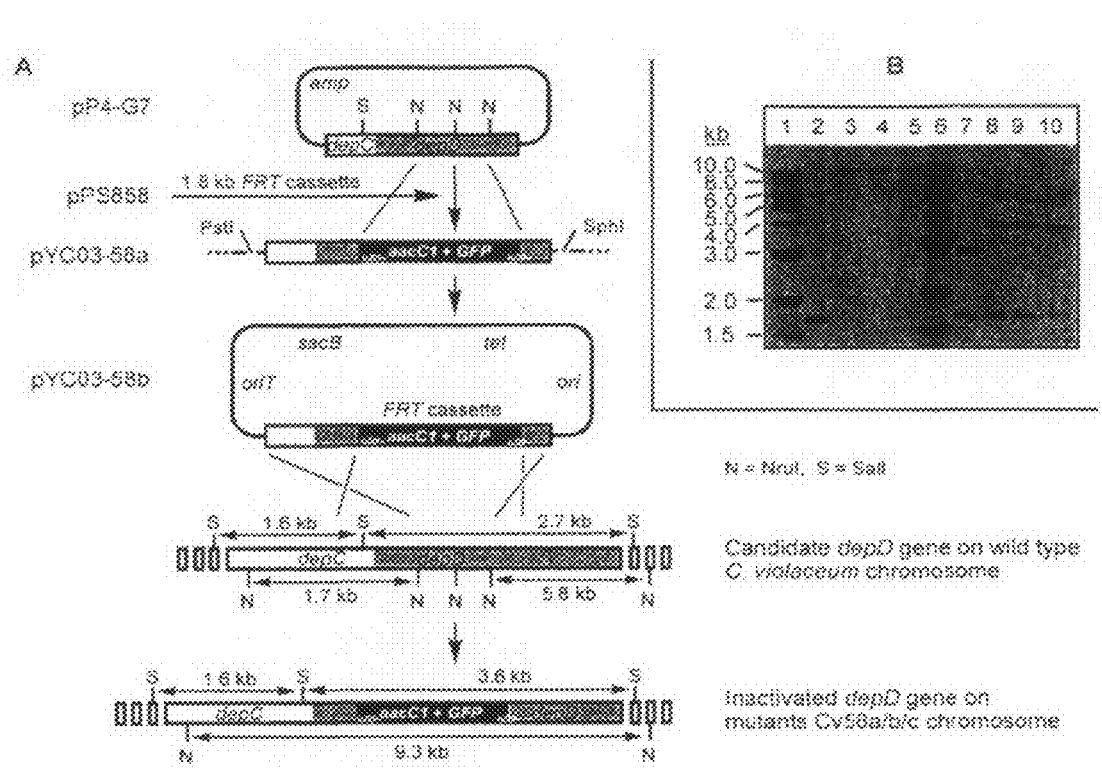
FIG. 3 depicts the method for creation of depD (SEQ ID NO: 34)-inactivated mutant strains by targeted gene replacement.

To inactivate the P4-G7-SP6-associated depD gene (depD (SEQ ID NO: 34) was chosen as an example for full description here because it encodes part of a hybrid PKS-NRPS system that is of prime interest) (FIG. 3A), two internal NruI fragments (0.46 and 0.49 kb) of the pP4-G7 insert were removed and replaced by a 1.8-kb SmaI fragment of the FRT cassette from pPS858 to make an intermediate construct, pYC03-58a. A 3.7-kb PstI/SphI fragment containing the FRT cassette with flanking DNAs from pYC03-58a was recovered, end repaired, and inserted into the SmaI site of pEX18Tc to make a final construct, pYC03-58b. Plasmid pYC03-58b was introduced into *E. coli* S17-1 cells and subsequently transferred into *C. violaceum* cells by conjugation. In the designed selection medium (see Materials and Methods), Ap at a concentration of 200 µg/ml suppresses the growth of *E. coli* S17-1 cells, Gm at a concentration of 50 µg/ml selects for the presence of the FRT cassette, and sucrose at a concentration of 5% counterselects for the loss of a functional sacB$^+$ gene on the vector. Collectively, this experiment strongly selected for double-crossover mutants of *C. violaceum* with part of the targeted depD (SEQ ID NO: 34) replaced by the FRT cassette. Hundreds of exconjugants appeared on a typical selection plate after incubation at 30° C. for 2 days. The efficiency of conjugation and gene recombination was estimated to be in the range from $10^{-6}$ to $10^{-5}$ per cell.

Southern analysis (FIG. 3B) clearly showed that when genomic DNA of *C. violaceum* strains was digested with NruI (lanes 2 to 5), the wild type strain showed two bands (1.7 and 5.8 kb; 0.46- and 0.49-kb DNA fragments ran off the gel during electrophoresis) that hybridized to the probe made from the 2.6-kb insert of pP4-G7. Considering that there are three internal NruI sites in the 2.6-kb insert of pP4-G7 and that one central NruI site was removed and two other sites were destroyed during the construction of pYC03-58a, insertion of the 1.8-kb FRT cassette via double-crossover DNA recombination was expected to result in a 9.3-kb (1.7 kb+5.8 kb+1.8 kb) hybridized band in the mutant genotype. Three out of eight random exconjugants were proven in this experiment to have the correct genotype and they were designated independent depD (SEQ ID NO: 34)-inactivated mutant strains Cv58a, Cv58b and Cv58c (collectively designated the Cv58a/b/c mutants). Similarly, when genomic DNA was digested with SalI (lanes 7 to 10), the size of a 2.7-kb hybridized band in the wild-type strain increased to 3.6 kb (2.7 kb−0.49 kb−0.46 kb+1.8 kb) in the mutant strains, as expected. The 1.6-kb band in the wild-type strain remained unchanged in mutant strains because the DNA fragment is located outside the gene replacement region.

The same strategy was used to inactivate the P3-A6-SP6-associated gene (not named) and the P4-B4-SP6-associated depD gene (3'-part), to create mutant strains Cv56a/b/c and Cv57a/b/c, respectively, and their genotypes were verified by Southern analyses as well (data not shown).

During the course of method development, two other conjugation systems were also tested. One method used the methylation-deficient *E. coli* ET12567(pUZ8002) (MacNeil, Gewain et al. 1992; Kieser, Bibb et al. 2000) and the other used *E. coli* MT607(pRK600) (Finan, Kunkel et al. 1986) as donor strains to mobilize a conjugation construct (such as pYC03-58b) into *C. violaceum* cells. Both systems generated exconjugants, but they were at least 10-fold less efficient than the *E. coli* S17-1 strain-mediated conjugation between *E. coli* and *C. violaceum* cells (data not shown). In addition, it was noticed that, since the FRT cassette contains a functional GFP gene that encodes the green fluorescent protein (GFP), *E. coli* and *C. violaceum* colonies or cultures with the FRT cassette present on a replicable plasmid or integrated into chromosome were distinguishable from the wild-type bacteria by a greenish color (data not shown). Therefore, bacterial exconjugants carrying the FRT cassette could be identified by direct observation or by a simple GFP assay. Furthermore, the marker genes (aacC1 and GFP in the FRT cassette) integrated into the mutant chromosome could be excised precisely by a FLP recombinase encoded by pFLP2 plasmid in the Flp-FRT system to create unmarked mutants (Hoang, Karkhoff-Schweizer et al. 1998). Unmarked mutants could be mutated at different loci sequentially to create multiple gene deletions or gene replacements. This feature could be very useful for future pathway engineering and combinatorial biosynthesis studies.

Figure 4:
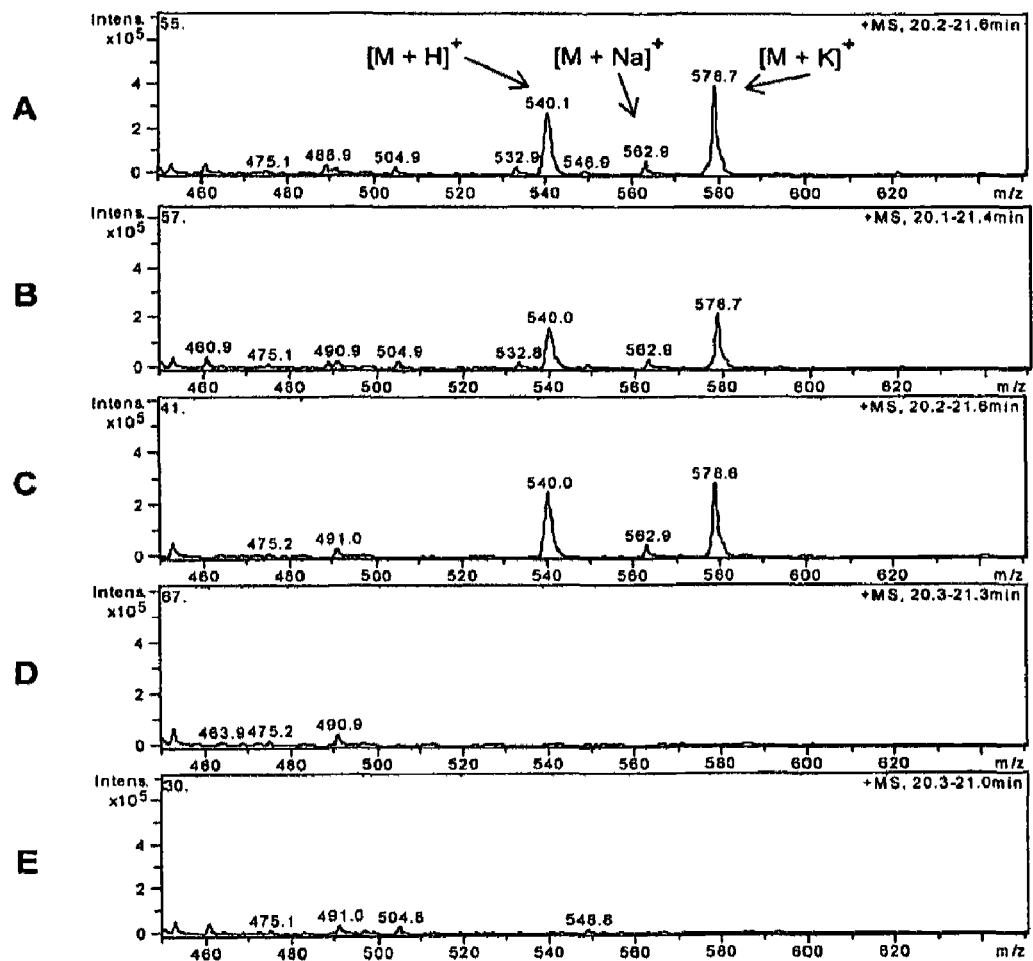
FIG. 4 is a set of graphs showing detection of FK228 positive ion signals by LC-MS. Samples were obtained from an authentic FK228 standard (A), wild-type C. violaceum (B), Cv56a/b/c mutants with the pP3-A6-associated gene inactivated (C), Cv57a/b/c mutants with the pP4-B4-associated depD (SEQ ID NO: 34) gene (3'-part) inactivated (D), and Cv58a/b/c mutants with the pP4-G7-associated depD (SEQ ID NO: 34) gene inactivated (E). For each mutation three mutants (a, b, and c) yielded identical results; therefore, only one data profile for each mutation is presented.

Confirmation of the necessity of the depD (SEQ ID NO: 34) gene for FK228 biosynthesis in *C. violaceum* No. 968. The FK228 productivity of the wild-type and mutant (Cv56a/b/c, Cv57a/b/c and Cv58a/b/c) strains of *C. violaceum* was examined by fermentation and LC-MS analysis. FK228 does not produce a characteristic UV spectrum because it lacks a chromophore, but its positive ion signals are strong and appeared near 20.8 min under the chromatographic conditions tested (FIG. 4). The calculated positive ion signal of FK228 is [M+H]$^+$ at m/z 541.2, and its ion adducts are [M+Na]$^+$ at m/z 563.2 and [M+K]$^+$ at m/z 580.2 for an authentic FK228 sample, but actual observed signals were m/z 540.1, m/z 562.9, and m/z 578.7, respectively. The small mass differences between the calculated and the observed values were likely due to inadequate instrument calibration. The samples from wild-type and Cv56a/b/c mutant strains yielded almost the same signals as the authentic FK228. However, no FK228 ion signal was detected in samples from Cv57a/b/c/ or Cv58a/b/c/ mutant strains. These results suggest that inactivation of depD (SEQ ID NO: 34), but not inactivation of the P3-A6-SP6-associated gene, completely abolished FK228 production, which confirmed the necessity of depD (SEQ ID NO: 34) for FK228 biosynthesis in *C. violaceum* No. 968.

Cloning, sequencing, and in silico analysis of the FK228 biosynthetic (dep) gene cluster (SEQ ID NO: 1). A series of overlapping cosmid clones were obtained by colony hybridization with digoxigenin-labeled insert DNA of pP4-G7 as a probe. Cosmid end sequencing indicated that, among those clones, cosmid 18 appears to contain the entire dep gene cluster (SEQ ID NO: 1); therefore, the nucleotide sequence of cosmid 18 was determined by shotgun method, which revealed a 40,434-bp contig (FIG. 2A). Due to concern about the irregularity of the deduced protein domain organizations (see below for details), cosmid 2, which covers most, but not all of, the dep gene cluster, was also sequenced by a subcloning and primer walking strategy (FIG. 2A). A cosmid clone carrying a partial dep gene cluster was chosen for sequencing verification purposes because a partial gene cluster cloned from the gram-negative bacterium *C. violaceum* into another gram-negative bacterium, *E. coli*, should not result in acquired toxicity, minimizing possible gene deletion or recombination. The sequences of the overlapped region between cosmid 18 and cosmid 2 agreed perfectly, confirming the shotgun sequence quality and reliability.

The assembled contig contains 21 apparent genes or open reading frames (ORFs) (two partial sequences at the ends) (Table 3 and FIG. 2A). Bioinformatic analyses further predicted that the dep gene cluster (SEQ ID NO: 1) consists of 14 genes, designated depA (SEQ ID NO: 28) through depN (SEQ ID NO: 26), flanked by several housekeeping genes (orf1 (SEQ ID NO: 14) through orf3 (SEQ ID NO: 18) and orf18 (SEQ ID NO: 48) through orf21 (SEQ ID NO: 54)), although the exact boundaries of the dep gene cluster (SEQ ID NO: 1) have not been experimentally verified yet. The flanking housekeeping genes have homology with genes in a single region of the C. violaceum ATCC 12472 genome (CV_3375 through CV_3386) (Consortium 2003).

Interestingly, five ATCC 12472 genes ($CV_{\_b\,3379}$ through CV_3383) are seemingly replaced by the dep gene cluster (SEQ ID NO: 1), suggesting that a lateral gene transfer event occurred (Ochman, Lawrence et al. 2000). Further evidence that supports this notion comes from a G+C content analysis. The flanking housekeeping genes have an average G+C content of 62.9%, while the dep gene cluster (SEQ ID NO: 1) has a G+C content of 69.0%. C. violaceum No. 968 could have acquired the dep gene cluster (SEQ ID NO: 1) from an organism with a higher-G+C genome at the expense of a five-gene deletion of its own.

Cotranscription is common among related genes in bacteria. In the dep gene cluster (SEQ ID NO: 1) and flanking regions, orf1 (SEQ ID NO: 14) through orf3 (SEQ ID NO: 18), orf18 (SEQ ID NO: 48) through orf21 (SEQ ID NO: 54), depABCDEFGH (SEQ ID NOS: 28, 30, 32, 34, 36, 38, 40, and 42), and depIJ (SEQ ID NOS: 44 and 46) are very likely organized as operons, respectively, because genes within each putative operon have overlapping stop and start codons. In contrast, genes depK (SEQ ID NO: 20), depL (SEQ ID NO: 22), depM (SEQ ID NO: 24), and depN (SEQ ID NO: 26) are separated by variable lengths of intergenic DNA. This analysis facilitated the prediction that depJ (SEQ ID NO: 46) is the downstream boundary of the dep gene cluster (SEQ ID NO: 1) because orf18 (SEQ ID NO: 48) through orf21 (SEQ ID NO: 54) are housekeeping genes in a single putative operon.

Model for FK228 biosynthesis by a hybrid NRPS-PKS-NRPS assembly line. Many natural products are often biosynthesized by modular NPRSs, PKSs, or hybrid NRPS-PKS or PKS-NRPS assembly lines in a colinearity model in which the substrate specificity and the number and order of modules dictate the chemical makeup of the products (for recent comprehensive reviews, see references (Finking and Marahiel 2004; Fischbach and Walsh 2006; Hill 2006); meanwhile, variations from the canonical model, including colinearity violation, iterative polymerization (iteration), missing or misplacing domains, module skipping or stuttering, stand-alone domains, alternative chain termination, the presence of unique domains, or trans-acting enzymes, have all been documented in individual biosynthetic pathways [for recent comprehensive reviews, see references (Shen 2003; Wenzel and Muller 2005; Fischbach and Walsh 2006). Based on extensive bioinformatics analyses of the domain and module organization of biosynthetic enzymes encoded by the dep gene cluster (SEQ ID NO: 1), a model for FK228 biosynthesis by a hybrid NRPS-PKS-NRPS assembly line is proposed (FIG. 2B), and this model should serve as a general guideline for future studies and experimental validation. The proposed pathway includes nine proteins (DepA (SEQ ID NO: 29), DepB (SEQ ID NO: 31), DepC (SEQ ID NO: 33), DepD (SEQ ID NO: 35), DepE (SEQ ID NO: 37), DepF (SEQ ID NO: 39), DepH (SEQ ID NO: 43), and DepM (SEQ ID NO: 25), as well as DepJ (SEQ ID NO: 47) [not drawn in the model]) that constitute five NRPS modules, two PKS modules, and accessory activities; each module is responsible for the incorporation of one contributing building block.

Based on the model, FK228 biosynthesis starts with the activation of a Cysteine by the A domain in module 1 to form a cysteinyl-S-PCP intermediate. DepM (SEQ ID NO: 25) (an aminotransferase) is proposed to act in trans to remove an amino group from the intermediate to form 4-mercaptobutanyl-S-PCP. Aminotransferase domains have been found to be an integral part of the PKSs in the biosynthesis of mycosubtilin (Duitman, Hamoen et al. 1999) and iturin A (Tsuge, Akiyama et al. 2001), adding an amino group; no such domain, however, has been found to remove an amino group in a reverse reaction. The C domain in module 1 appears to be nonfunctional because of a lack of a critical catalytic motif, HHXXXDG (SEQ ID NO: 7); a nonfunctional C domain disconnects the possible chemical interaction between the upstream acyl coenzyme A ligase (AL) domain and the downstream A domain.

Next, PKS modules 2 and 3 sequentially extend the growing chain with two $C_2$ units from MCoA. However, module 2 contains only a remnant nonfunctional AT domain that lacks essential motifs (e.g., GHSXG (SEQ ID NO. 8) and A[FS]HS (SEQ ID NO. 9)), and module 3 lacks an AT domain. The dehydratase (DH) domain in modules 2 and 3 also appear to be nonfunctional because of a lack of a conserved active site motif, HXXXGXXXXP (SEQ ID NO. 10). An unknown stand-alone AT-DH didomain protein (or, alternatively, discrete AT and DH proteins) is proposed to act in trans to compensate the modules in the PKS mode of biosynthesis. Furthermore, since no gene encoding a stand-alone AT-DH didomain is present in the dep gene cluster (SEQ ID NO: 1), it must exist in another region of the genome. Stand-alone AT domains or AT-X didomains (where X is any domain) have been identified in recent years in the biosynthetic pathways of natural products, including leinamycin (Cheng, Tang et al. 2003), pederin (Piel 2002), and many other compounds. A recent molecular cellular study of the bacillaene biosynthetic enzyme complex revealed an amazing interaction between a stand-alone AT-X didomain and the rest of a mega-PKS complex in Bacillus subtilis (Straight, Fischbach et al. 2007).

In addition, DepF (SEQ ID NO: 39), an FadE2-like acyl coenzyme A dehydrogenase, has been proposed to act in trans on module 2 to generate a double bond on the β-hydroxyl-5-mercaptopentanoyl-S-ACP intermediate to form the β-5-mercaptopent-2-enoyl-S-ACP intermediate. If this is true, DepF (SEQ ID NO: 39) would be functionally equivalent to an enoylreductase (ER). KR domains in modules 2 and 3, although intact, are proposed to be inactive, probably due to a lack of proper interaction with the putative in trans-acting AT-DH didomain. Modules 4, 5, and 6 extend the growing intermediate chain with activated D-Val, D-Cys, and 2,3-dehydro-2-aminobutanoic acid (Dhb) (2,3-dehydrothreonine—Dht) sequentially in the canonical model of the NRPS mode of biosynthesis. Module 7 is expected to incorporate a Val, but an A domain is completely missing in this module. It is proposed that the A domain in module 4, which specifies a Val, acts in trans to aminoacylate the PCP domain in module 7. Such phenomenon has been observed in the biosynthetic pathways of viomycin (Thomas, Chan et al. 2003), yersiniabactin (Gehring, DeMoll et al. 1998), and other compounds.

Finally, terminal thioesterase (TE) on DepE (SEQ ID NO: 37) should catalyze the formation of an ester linkage between a hydroxyl group originated from MCoA and an β-keto group from Val to form a 16-membered macrolactone ring. In addition, a flavin adenine dinucleotide (FAD)-dependent pyridine nucleotide-disulfide oxidoreductase encoded by depH is proposed to bring the free sulfhydryl groups from two Cys residues together and to form an intramolecular disulfide bond. Disulfide bond formation hallmarks the formation of a 17-membered ring structure and brings the FK228 biosynthesis to completion. DepJ (SEQ ID NO: 47), a discrete type II TE, is not drawn into the model, and type II TEs are generally believed to have a proofreading function during chain elongation to ensure smooth biosynthesis by selectively removing misprimed thioesters or shunt-intermediates (Heathcote, Staunton et al. 2001). It is necessary to point out that, in the model described above, several unique features that include the trans-acting DepM (SEQ ID NO: 25), DepF (SEQ ID NO: 39), an unknown stand-alone AT-DH didomain and a trans-acting A domain are speculative and require further experimental validation.

Other genes in the dep gene cluster (SEQ ID NO: 1). There are two apparent resistance genes in the dep gene cluster (SEQ ID NO: 1). An esterase/lipase, encoded by depI (SEQ ID NO: 44), is proposed to hydrolyze the ester linkage and/or the disulfide bond in FK228 to prevent the accumulation of excess concentration of FK228 in cells where FK228 may become toxic. A phosphotransferase, encoded by depG (SEQ ID NO: 40), is proposed to further mask and quench the hydrolyzed FK228 by adding a phosphate group to the freed hydroxyl and/or sulfhydroxyl group(s).

Surprisingly, no gene encoding exportation machinery is found in the dep gene cluster (SEQ ID NO: 1). The depL (SEQ ID NO: 22) gene encodes a typical transcriptional regulator that contains a helix-turn-helix motif, indicting its DNA-binding activity. The depK (SEQ ID NO: 20) gene encodes a conserved functionally unknown protein. Finally, depN (SEQ ID NO: 26) encodes a nonfunctional PCP remnant without a critical serine residue in a conserved motif GX(HD)S (SEQ ID NO. 11), necessary for phosphopantetheinylation and covalent substrate aminoacylation.

Discovery of FK228 Analogs (Thailandepsins) from *Burkholderia thailandensis* E264

Figure 5:
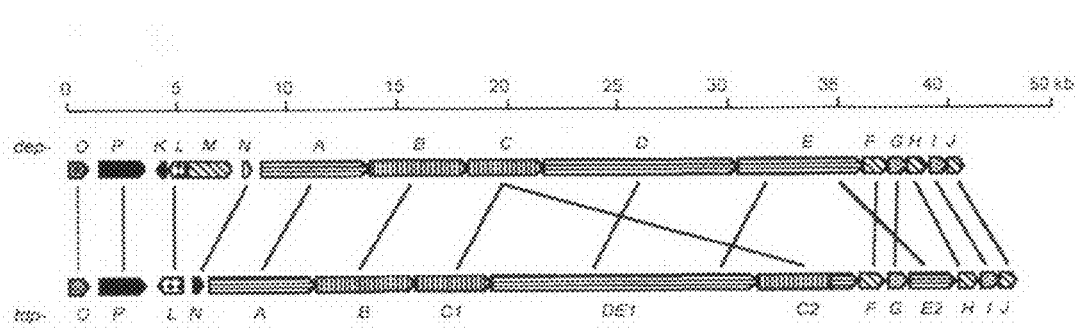
FIG. 5 depicts a comparative map of the FK228 biosynthetic (dep) gene cluster (SEQ ID NO: 1) and the thailandepsin biosynthetic (tdp) gene cluster (SEQ ID NO: 2). Gene pattern codes: NRPS genes in dark horizontal strips, PKS genes in dark vertical strips, accessory biosynthetic genes in dark upward diagonal pattern, resistance genes in zigzag pattern, regulatory gene in solid diamond, genes with unknown functions in solid black, inactive genes in white. Solid lines connect genes with both sequence similarity and functional similarity (homologs). Dotted lines connect genes with only functional similarity.
Figure 6:
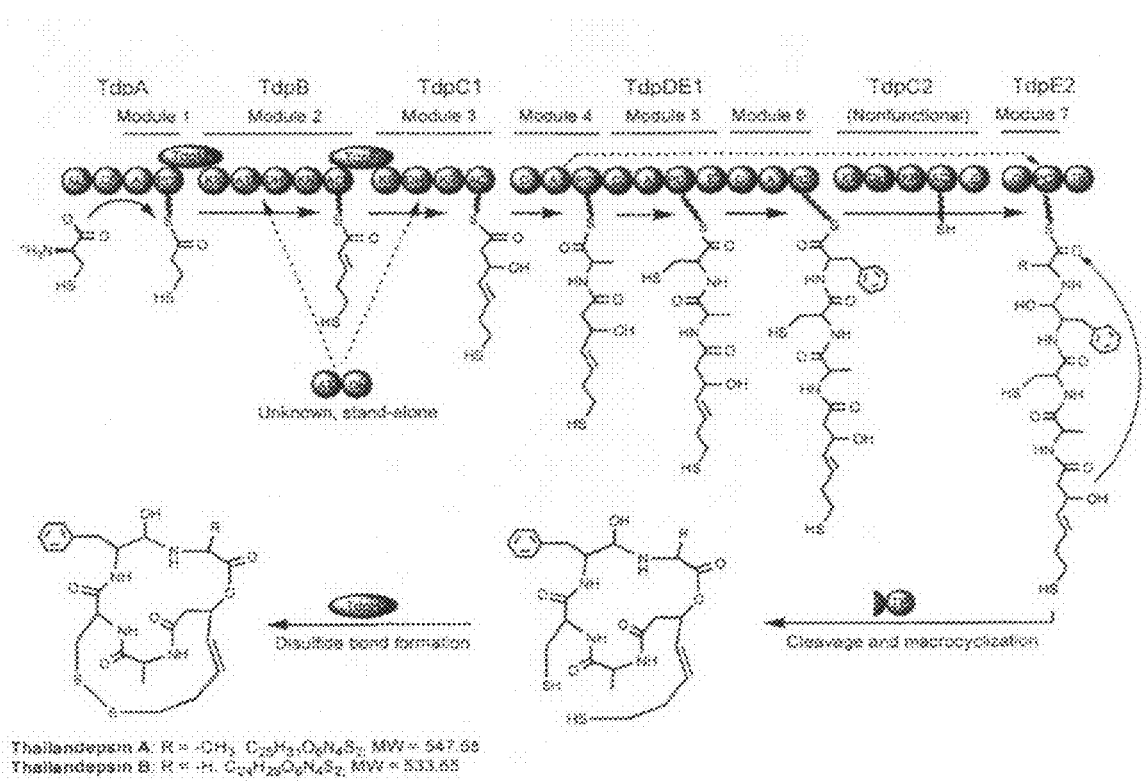
FIG. 6 depicts a model for the biosynthesis of thailandepsins. In this model, six known proteins (TdpA (SEQ ID NO: 79), TdpB (SEQ ID NO: 77), TdpC1 (SEQ ID NO: 75), TdpDE1 (SEQ ID NO: 73), TdpE2 (SEQ ID NO: 65), TdpF (SEQ ID NO: 69), and TdpH (SEQ ID NO: 63)) and two putative stand-alone proteins (TdpM and AT-DH) constitute a hybrid NRPS-PKS-NRPS assembly line that sequentially polymerizes building blocks (oligomers) into complex mature products. TdpC2 (SEQ ID NO: 71) appears nonfunctional.
Figure 7:
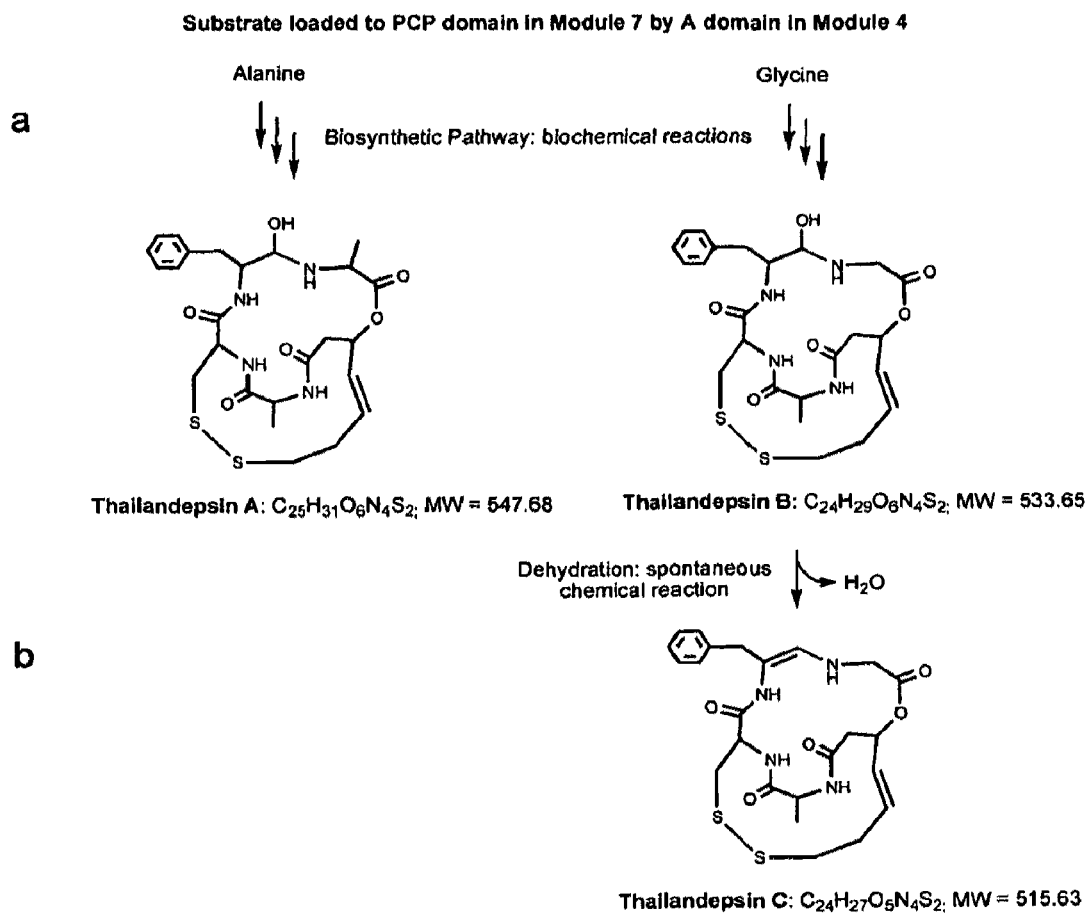
FIG. 7 depicts the proposed mechanisms for the biosynthesis of thailandepsins A and B and the conversion of thailandepsin B to thailandepsin C.
Figure 8:
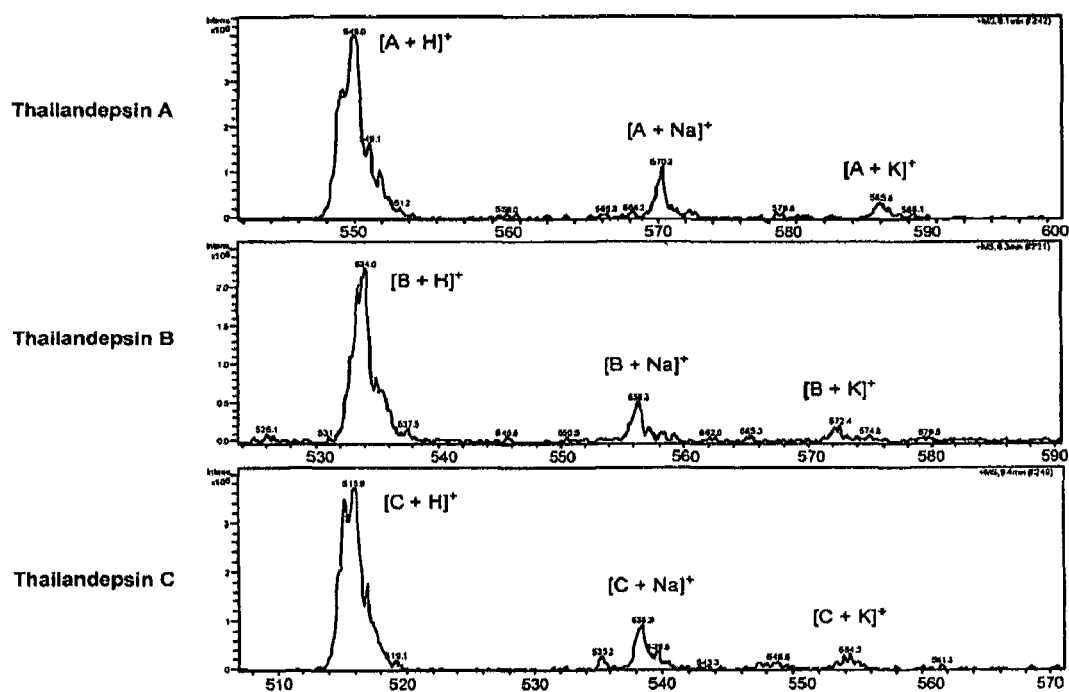
FIG. 8 shows graphs depicting the LC-MS positive ion signals of thailandepsin A, B or C, respectively.

The cloning and characterization of the FK228 biosynthetic gene cluster (Cheng, Yang et al. 2007) lead to the identification of a biosynthetic gene cluster (designated tdp for thailandepsin) in the genome of *Burkholderia thailandensis* E264 (GenBank accession no. CP000085 and CP000086). The gene and deduced protein organizations of this tdp gene cluster (SEQ ID NO: 2) resemble those of the dep gene cluster (SEQ ID NO: 1) (FIG. 5 and Table 4). Bioinformatics and cheminformatics tools were used to dissect the gene and deduced protein organizations of the tdp gene cluster (SEQ ID NO: 2) and predicted putative chemical structures of thailandepsins. Further experiments have purified and partially identified three compounds produced by the thailandepsin pathway (FIG. 6, FIG. 7 and FIG. 8). It is expected that the thailandepsins may have activities similar to FK228.

TABLE 4

Comparison of the Deduced Proteins of Thailandepsin Biosynthetic (tdp) Gene Cluster with Those of FK228 Biosynthetic (dep) Gene Cluster (SEQ ID NO: 1)

| Gene annotation in GenBank | tdp Gene Cluster | | Comparison % | dep Gene Cluster | |
|---|---|---|---|---|---|
| | Deduced protein (size$^a$) | Proposed function$^b$ | Identity/Similarity between two proteins | Deduced protein (size$^a$) | Proposed function$^b$ |
| — | — | — | — | DepK (SEQ ID NO: 21) (85) | Conserved protein, function unknown |
| BTH_I2369 | TdpL (368) | Transcriptional regulator, AraC family | — | DepL (SEQ ID NO: 23) (155) | Transcriptional regulator, MarR family |
| — | — | — | — | DepM (SEQ ID NO: 25) (389) | Aminotransferase, class I and II |
| BTH_I2368 | TdpN (SEQ ID NO: 81) (69) | ArCP | — | DepN (SEQ ID NO: 27) (65) | PCP$^a$ |
| BTH_I2367 | TdpA (SEQ ID NO: 79) (1699) | NRPS: AL$^i$-C$^a$-A$_{Cys}$-PCP | 73/82 | DepA (SEQ ID NO: 29) (1697) | NRPS: AL$^i$-C$^a$-A$_{Cys}$-PCP |
| BTH_I2366 | TdpB (SEQ ID NO: 77) (1560) | PKS: KS-AT$^a$-DH$^a$-KR$^i$-ACP | 77/85 | DepB (SEQ ID NO: 31) (1553) | PKS: KS-AT$^a$-DH$^a$-KR$^i$-ACP |
| BTH_I2365 | TdpC1 (SEQ ID NO: 75) (1184) | PKS: KS-DH$^a$-KR$^i$-ACP | 75/83 | DepC (SEQ ID NO: 33) (1183) | PKS: KS-DH$^a$-KR$^i$-ACP |
| BTH_I2364 | TdpDE1 (SEQ ID NO: 73) (3650) | NRPS: C-A$_{Ala}$-PCP-C-A$_{Cys}$-PCP-E-C-A$_{Tyr-D}$-PCP | 48/58$^f$ | DepD (SEQ ID NO: 35) (3057) | NRPS: C-A$_{Val}$-PCP-E-C-A$_{Cys}$-PCP-E |
| — | — | — | — | DepE (SEQ ID NO: 37) (1892) | NRPS: C-A$_{Dbb}$-PCP-C-PCP-TE |
| BTH_I2363 | TdpC2 (SEQ ID NO: 71) (1525) | PKS: KS-DH$^a$-KR$^i$-ACP-E | 31/41$^g$ | | |
| BTH_I2362 | TdpF (SEQ ID NO: 69) (390) | FadE2-like acyl-CoA dehydrogenase | 89/94 | DepF (SEQ ID NO: 39) (390) | FadE2-like acyl-CoA dehydrogenase |
| BTH_I2361 | TdpG (SEQ ID NO: 67) (322) | Phosphotransferase | 75/84 | DepG (SEQ ID NO: 41) (321) | Phosphotransferase |

TABLE 4-continued

Comparison of the Deduced Proteins of Thailandepsin Biosynthetic (tdp) Gene
Cluster with Those of FK228 Biosynthetic (dep) Gene Cluster (SEQ ID NO: 1)

| Gene annotation in GenBank | tdp Gene Cluster | | Comparison % | dep Gene Cluster | |
|---|---|---|---|---|---|
| | Deduced protein (size[a]) | Proposed function[b] | Identity/Similarity between two proteins | Deduced protein (size[a]) | Proposed function[b] |
| BTH_I2360 | TdpE2 (SEQ ID NO: 65) (743) | C-PCP-TE | 32/49[h] | — | — |
| BTH_I2359 | TdpH (SEQ ID NO: 63) (324) | FAD-dependent pyridine nucleotide-disulphide oxidoreductase | 72/85 | DepH (SEQ ID NO: 43) (319) | FAD-dependent pyridine nucleotide-disulphide oxidoreductase |
| BTH_I2358 | TdpI (SEQ ID NO: 61) (306) | Putative esterase/Lipase | 74/84 | DepI (SEQ ID NO: 45) (304) | Putative esterase/Lipase |
| BTH_I2357 | TdpJ (SEQ ID NO: 59) (278) | Type II thioesterase | 67/80 | DepJ (SEQ ID NO: 47) (254) | Type II thioesterase |

[a]Number of amino acids;
[b]abbreviations are defined in text; subscript indicates the substrate specificity of enzymes;
[f]the first 1489 aa;
[g]first 1174 aa between TdpC2 (SEQ ID NO: 71) and DepC (SEQ ID NO: 33);
[h]first 367 aa of TdpE2 (SEQ ID NO: 65) and DepE (SEQ ID NO: 37) C-terminal end;
[i]inactive;
[n]nonfunctional.

Bacterial strains and plasmids. *Burkholderia thailandensis* E264 (ATCC 700388; a gram-negative motile rod bacterial species isolated from a rice paddy in Thailand; $Am^R$ $Km^R$ $Gm^R$ $Sm^R$ $Pm^R$ $Tc^S$) and *E. coli* were routinely cultured in Luria-Bertani (LB) broth or on LB agar at 37° C. For the construction of a targeted gene-disruption mutant, a suicide vector, pEX18Tc ($Tc^R$ $oriT^+$ $sacB^+$, conjugative), originally developed for *Pseudomonas aeruginosa* genetics (Hoang, Karkhoff-Schweizer et al. 1998), was adopted and applied successfully in *B. thailandensis*.

Construction of a targeted gene-disruption mutant of *B. thailandensis*. General DNA manipulations, including plasmid preparation, restriction enzyme digestion, agarose gel electrophoresis, and bacterial transformation, were performed according to standard protocols (Sambrook and Russell 2000) or the manufacturer's instructions (New England BioLabs). Genomic DNA of the wild-type or mutant strain of *B. thailandensis* was prepared from an overnight culture with an UltraClean microbial DNA isolation kit (MO BIO Labs). An internal DNA fragment of tdpA (SEQ ID NO: 78) was amplified from *B. thailandensis* genomic DNA with the following PCR primers: TdpA-KO-FP1, 5'-AGGTACCGCCTACGTGATCTTCACG-3' (SEQ ID NO. 12), containing a KpnI site (underlined); and TdpA-KO-RP1, 5'-CTAAGCTTGACCTGGCCGTCCATCC-3' (SEQ ID NO. 13), containing a HindIII site (underlined). Amplified product was purified from the PCR mixture with a QIAGEN PCR Purification kit, double digested with KpnI and HindIII, separated and re-purified from an agarose gel. A final 760-bp KpnI-HindIII product was cloned into the KpnI-HindIII sites of pEX18Tc to yield a gene disruption construct pDZ01-69a6. This construct was first transformed into *E. coli* S17-1 cells and then transferred into *B. thailandensis* cells by bacterial interspecies conjugation as follows.

Two bacterial strains, *E. coli* S17-1 (pDZ01-69a6) and *B. thailandensis*, were grown separately in 3 ml of LB medium supplemented with appropriate antibiotics (10 μg/ml tetracycline for *E. coli* S17-1 [pDZ01-69a6] and 50 μg/ml apramycin for *B. thailandensis*) at 37° C. with shaking until the late mid-log phase (6 to 8 h). Cells from 1 ml of each culture were collected by centrifugation at 4,000×g for 15 min at 4° C., and the cell pellets were washed once with 1 ml LB medium. Each cell pellet was finally resuspended in 100 μl of LB. Cell suspensions of two bacterial strains were then pooled and spread evenly on a wet 0.45-μm nitrocellulose membrane (Whatman) on LB agar supplemented with 10 mM $MgSO_4$. After the plate had been incubated at 30° C. for 12 h to 16 h, the membrane seeded with bacteria was used to print several LB agar plates containing 100 μg/ml tetracycline and 50 μg/ml apramycin to select for vector-integrated mutant strain (designated Bth69a6; tdpA::pEX18Tc; $Tc^R$ $Am^R$). The correct integration of nonreplicative vector pEX18Tc into the *B. thailandensis* chromosome via homologous DNA recombination was examined and confirmed by PCR analysis.

Examination of the metabolic differences between wild-type and the Bth69a6 mutant strain of *B. thailandensis*. Gene tdpA (SEQ ID NO: 78) is proposed to be involved in the biosynthesis of thailandepsins (FIG. 5 and FIG. 6). Therefore, disruption of tdpA (SEQ ID NO: 78) should abolish the production of thailandepsins in the mutant strain. Detection of the metabolic profiles between wild-type and the Bth69a6 mutant strain of *B. thailandensis* should facilitate the identification and purification of thailandepsins.

LC-MS analysis of crude extracts from the fermentation broths of wild-type and the Bth69a6 mutant strain of *B. thailandensis* revealed that three ion signals ([M+H]+ m/z 548.0, 534.0, and 515.9, respectively) were present in the crude extract of wild-type strain but were absent in the crude extract of Bth69a6 mutant strain (data not shown). This experiment indicated that disruption of tdpA (SEQ ID NO: 78) gene resulted in the loss of production of three putative compounds in the mutant strain, and thus established a causal relationship between the genotype (tdpA (SEQ ID NO: 78) gene) and the phenotype (production of three putative natural products).

Purification and identification of thailandepsins. Wild-type *B. thailandensis* E264 strain was fermented in a modified nutrient broth (1.0% glucose, 1.0% Difco nutrient broth, 0.5% NaCl, 0.1% $CaCO_3$, pH 7.0) (8×500 ml) and in a modified YM-254890 medium (2.0% glycerol, 0.5% glucose, 0.5% peptone, 0.1% yeast extract, 0.1% NaCl, pH 7.0)

(8×500 ml) at 37° C. for 4 days with shaking (160 rpm). Sterile resins, HP-20 and XAD-4 (for absorbing secreted metabolites), were added to culture to a final concentration of 2.5% (w/v) each at day 2. Resins and cells were collected at the end of fermentation by centrifugation and subsequently freeze-dried for 2 days. The dry mass was extracted with two volumes of methanol (w/v). Methanol extracts from two fermentation media were combined at this point and the solvent was removed under reduced pressure to give a crude extract. The crude extract was redissolved in methanol, fractionated and eluted by methanol through a Sephadex LH20 column, and four parts (B-1, B-2, B-3 and B-4) were collected manually, according to distinctive color zones. Part B-3 was further fractionated and eluted through a Sephadex LH20 column, to yield three fractions (B-3-1, B-3-2 and B-3-3). Fraction B-3-3 was then separated by preparative HPLC through an Rp-18 column (5 μm particles, 35 mm×250 mm) with a linear gradient (180 min from 15% to 60% methanol) and a flow rate of 7 ml/min. UV absorption signals were recorded at 210 nm wavelength by a diode array detection.

Three thailandepsin peaks were collected within 120 to 150 min of elution time window. Solvent was evaporated under reduced pressure and the purified thailandepsin samples were subjected to MS analysis (FIG. 8). The detected m/z values were used to correct the structure predictions of thailandepsins A and B (FIG. 6), and to postulate the spontaneous chemical conversion of thailandepsin B to thailandepsin C (FIG. 7).

REFERENCES

Acharya, M. R., A. Sparreboom, et al. (2005). "Rational development of histone deacetylase inhibitors as anticancer agents: a review." *Mol Pharmacol* 68(4): 917-32.

Altschul, S. F., W. Gish, et al. (1990). "Basic local alignment search tool." *J Mol Biol* 215(3): 403-10.

Ansari, M. Z., G. Yadav, et al. (2004). "NRPS-PKS: a knowledge-based resource for analysis of NRPS/PKS megasynthases." *Nucleic Acids Res* 32(Web Server issue): W405-13.

Bernstein, B. E., A. Meissner, et al. (2007). "The mammalian epigenome." *Cell* 128(4): 669-81.

Bolden, J. E., M. J. Peart, et al. (2006). "Anticancer activities of histone deacetylase inhibitors." *Nat Rev Drug Discov* 5(9): 769-84.

Byrd, J. C., C. Shinn, et al. (1999). "Depsipeptide (FR901228): a novel therapeutic agent with selective, in vitro activity against human B-cell chronic lymphocytic leukemia cells." *Blood* 94(4): 1401-8.

Challis, G. L., J. Ravel, et al. (2000). "Predictive, structure-based model of amino acid recognition by nonribosomal peptide synthetase adenylation domains." *Chem Biol* 7(3): 211-24.

Cheng, Y. Q. (2006). "Deciphering the biosynthetic codes for the potent anti-SARS-CoV cyclodepsipeptide valinomycin in Streptomyces tsusimaensis ATCC 15141." *Chembiochem* 7(3): 471-7.

Cheng, Y. Q., G. L. Tang, et al. (2003). "Type I polyketide synthase requiring a discrete acyltransferase for polyketide biosynthesis." *Proc Natl Acad Sci USA* 100(6): 3149-54.

Cheng, Y. Q., M. Yang, et al. (2007). "Characterization of a gene cluster responsible for the biosynthesis of anticancer agent FK228 in *Chromobacterium violaceum* No. 968." *Appl Environ Microbiol* 73(11): 3460-9.

Consortium, B. N. G. P. (2003). "The complete genome sequence of *Chromobacterium violaceum* reveals remarkable and exploitable bacterial adaptability." *Proc Natl Acad Sci USA* 100(20): 11660-5.

Dawson, S., J. P. Malkinson, et al. (2007). "Bisintercalator natural products with potential therapeutic applications: isolation, structure determination, synthetic and biological studies." *Nat Prod Rep* 24(1): 109-26.

Dokmanovic, M. and P. A. Marks (2005). "Prospects: histone deacetylase inhibitors." *J Cell Biochem* 96(2): 293-304.

Du, L., Y. Q. Cheng, et al. (2003). "Hybrid peptide-polyketide natural products: biosynthesis and prospects towards engineering novel molecules." *Genet Eng (NY)* 25: 227-67.

Duitman, E. H., L. W. Hamoen, et al. (1999). "The mycosubtilin synthetase of Bacillus subtilis ATCC6633: a multifunctional hybrid between a peptide synthetase, an amino transferase, and a fatty acid synthase." *Proc Natl Acad Sci USA* 96(23): 13294-9.

Duran, N. and C. F. Menck (2001). "Chromobacterium violaceum: a review of pharmacological and industiral perspectives." *Crit Rev Microbiol* 27(3): 201-22.

Finan, T. M., B. Kunkel, et al. (1986). "Second symbiotic megaplasmid in *Rhizobium meliloti* carrying exopolysaccharide and thiamine synthesis genes." *J Bacteriol* 167(1): 66-72.

Finking, R. and M. A. Marahiel (2004). "Biosynthesis of nonribosomal peptides1." *Annu Rev Microbiol* 58: 453-88.

Fischbach, M. A. and C. T. Walsh (2006). "Assembly-line enzymology for polyketide and nonribosomal Peptide antibiotics: logic, machinery, and mechanisms." *Chem Rev* 106(8): 3468-96.

Furumai, R., A. Matsuyama, et al. (2002). "FK228 (depsipeptide) as a natural prodrug that inhibits class I histone deacetylases." *Cancer Res* 62(17): 4916-21.

Garber, K. (2007). "HDAC inhibitors overcome first hurdle." *Nat Biotechnol* 25(1): 17-9.

Gehring, A. M., E. DeMoll, et al. (1998). "Iron acquisition in plague: modular logic in enzymatic biogenesis of yersiniabactin by Yersinia pestis." *Chem Biol* 5(10): 573-86.

Goldberg, A. D., C. D. Allis, et al. (2007). "Epigenetics: a landscape takes shape." *Cell* 128(4): 635-8.

Goll, M. G. and T. H. Bestor (2005). "Eukaryotic cytosine methyltransferases." *Annu Rev Biochem* 74: 481-514.

Grunewald, J. and M. A. Marahiel (2006). "Chemoenzymatic and template-directed synthesis of bioactive macrocyclic peptides." *Microbiol Mol Biol Rev* 70(1): 121-46.

Heathcote, M. L., J. Staunton, et al. (2001). "Role of type II thioesterases: evidence for removal of short acyl chains produced by aberrant decarboxylation of chain extender units." *Chem Biol* 8(2): 207-20.

Hill, A. M. (2006). "The biosynthesis, molecular genetics and enzymology of the polyketide-derived metabolites." *Nat Prod Rep* 23(2): 256-320.

Hoang, T. T., R. R. Karkhoff-Schweizer, et al. (1998). "A broad-host-range Flp-FRT recombination system for site-specific excision of chromosomally-located DNA sequences: application for isolation of unmarked Pseudomonas aeruginosa mutants." *Gene* 212(1): 77-86.

Johnstone, R. W. (2002). "Histone-deacetylase inhibitors: novel drugs for the treatment of cancer." *Nat Rev Drug Discov* 1(4): 287-99.

Kadokura, H., F. Katzen, et al. (2003). "Protein disulfide bond formation in prokaryotes." *Annu Rev Biochem* 72: 111-35.

Kieser, T., M. J. Bibb, et al. (2000). *Practical Streptomyces Genetics*. Norwich, England, John Innes Foundation.

Kouzarides, T. (2007). "Chromatin modifications and their function." *Cell* 128(4): 693-705.

Kouzarides, T. (2007). "SnapShot: Histone-Modifying Enzymes." *Cell* 131(4): 822.

Lee, C., H. Gorisch, et al. (1992). "A highly specific D-hydroxyisovalerate dehydrogenase from the enniatin producer Fusarium sambucinum." *J Biol Chem* 267(17): 11741-4.

Li, K. W., J. Wu, et al. (1996). "Total synthesis of the antitumor depsipeptide FR-901,228." *J Am Chem Soc* 118(30): 7237-38.

Lombo, F., A. Velasco, et al. (2006). "Deciphering the biosynthesis pathway of the antitumor thiocoraline from a marine actinomycete and its expression in two streptomyces species." *Chembiochem* 7(2): 366-76.

MacNeil, D. J., K. M. Gewain, et al. (1992). "Analysis of Streptomyces avermitilis genes required for avermectin biosynthesis utilizing a novel integration vector." *Gene* 111(1): 61-8.

Magarvey, N. A., M. Ehling-Schulz, et al. (2006). "Characterization of the cereulide NRPS alpha-hydroxy acid specifying modules: activation of alpha-keto acids and chiral reduction on the assembly line." *J Am Chem Soc* 128(33): 10698-9.

Mie Lee, Y., S. H. Kim, et al. (2003). "Inhibition of hypoxia-induced angiogenesis by FK228, a specific histone deacetylase inhibitor, via suppression of HIF-1alpha activity." *Biochem Biophys Res Commun* 300(1): 241-6.

Monneret, C. (2005). "Histone deacetylase inhibitors." *Eur J Med Chem* 40(1): 1-13.

Mootz, H. D., D. Schwarzer, et al. (2002). "Ways of assembling complex natural products on modular nonribosomal peptide synthetases." *Chembiochem* 3(6): 490-504.

Nakajima, H., Y. B. Kim, et al. (1998). "FR901228, a potent antitumor antibiotic, is a novel histone deacetylase inhibitor." *Exp Cell Res* 241(1): 126-33.

NCI (2008). NCI Drug Dictionary: clinical trials of romidepsin (FK228, FR901228, NSC 630176), National Cancer Institute. 2008.

Ochman, H., J. G. Lawrence, et al. (2000). "Lateral gene transfer and the nature of bacterial innovation." *Nature* 405(6784): 299-304.

Piekarz, R. and S. Bates (2004). "A review of depsipeptide and other histone deacetylase inhibitors in clinical trials." *Curr Pharm Des* 10(19): 2289-98.

Piel, J. (2002). "A polyketide synthase-peptide synthetase gene cluster from an uncultured bacterial symbiont of Paederus beetles." *Proc Natl Acad Sci USA* 99(22): 14002-7.

Pina, I. C., J. T. Gautschi, et al. (2003). "Psammaplins from the sponge *Pseudoceratina purpurea*: inhibition of both histone deacetylase and DNA methyltransferase." *J Org Chem* 68(10): 3866-73.

Rajgolikar, G., K. K. Chan, et al. (1998). "Effects of a novel antitumor depsipeptide, FR901228, on human breast cancer cells." *Breast Cancer Res Treat* 51(1): 29-38.

Reeves, C. D., S. Murli, et al. (2001). "Alteration of the substrate specificity of a modular polyketide synthase acyltransferase domain through site-specific mutations." *Biochemistry* 40(51): 15464-70.

Sambrook, J. and D. W. Russell (2000). *Molecular Cloning: a laboratory manual*. Cold Spring Harbor, N.Y., Cold Spring Harbor Laboratory.

Sandor, V., A. R. Robbins, et al. (2000). "FR901228 causes mitotic arrest but does not alter microtubule polymerization." *Anticancer Drugs* 11(6): 445-54.

Sandor, V., A. Senderowicz, et al. (2000). "P21-dependent g(1)arrest with downregulation of cyclin D1 and upregulation of cyclin E by the histone deacetylase inhibitor FR901228." *Br J Cancer* 83(6): 817-25.

Shen, B. (2003). "Polyketide biosynthesis beyond the type I, II and III polyketide synthase paradigms." *Curr Opin Chem Biol* 7(2): 285-95.

Shigematsu, N., H. Ueda, et al. (1994). "FR901228, a novel antitumor bicyclic depsipeptide produced by *Chromobacterium violaceum* No. 968. II. Structure determination." *J Antibiot (Tokyo)* 47(3): 311-4.

Simon, R., U. Priefer, et al. (1983). "A broad host range mobilisation system for in vivo genetic engineering: transposon mutagenesis in Gram-negative bacteria." *Bio/Technology* 1: 784-91.

Stachelhaus, T., H. D. Mootz, et al. (1999). "The specificity-conferring code of adenylation domains in nonribosomal peptide synthetases." *Chem Biol* 6(8): 493-505.

Straight, P. D., M. A. Fischbach, et al. (2007). "A singular enzymatic megacomplex from *Bacillus subtilis*." *Proc Natl Acad Sci USA* 104(1): 305-10.

Swaminathan, V., B. A. Reddy, et al. (2007). "Small molecule modulators in epigenetics: implications in gene expression and therapeutics." *Subcell Biochem* 41: 397-428.

Thomas, M. G., Y. A. Chan, et al. (2003). "Deciphering tuberactinomycin biosynthesis: isolation, sequencing, and annotation of the viomycin biosynthetic gene cluster." *Antimicrob Agents Chemother* 47(9): 2823-30.

Tsuge, K., T. Akiyama, et al. (2001). "Cloning, sequencing, and characterization of the iturin A operon." *J Bacteriol* 183(21): 6265-73.

Ueda, H., H. Nakajima, et al. (1994). "FR901228, a novel antitumor bicyclic depsipeptide produced by *Chromobacterium violaceum* No. 968. I. Taxonomy, fermentation, isolation, physico-chemical and biological properties, and antitumor activity." *J Antibiot (Tokyo)* 47(3): 301-10.

Ueda, H., H. Nakajima, et al. (1994). "Action of FR901228, a novel antitumor bicyclic depsipeptide produced by *Chromobacterium violaceum* No. 968, on Ha-ras transformed NIH3T3 cells." *Biosci Biotechnol Biochem* 58(9): 1579-83.

Vigushin, D. M. (2002). "FR-901228 Fujisawa/National Cancer Institute." *Curr Opin Investig Drugs* 3(9): 1396-402.

Walsh, C. T. (2002). "Combinatorial biosynthesis of antibiotics: challenges and opportunities." *Chembiochem* 3(2-3): 125-34.

Wang, L., S. Chen, et al. (2007). "Phosphorothioation of DNA in bacteria by dnd genes." *Nat Chem Biol* 3(11): 709-10.

Watanabe, K., K. Hotta, et al. (2006). "Total biosynthesis of antitumor nonribosomal peptides in Escherichia coli." *Nat Chem Biol* 2(8): 423-8.

Wenzel, S. C. and R. Muller (2005). "Formation of novel secondary metabolites by bacterial multimodular assembly lines: deviations from textbook biosynthetic logic." *Curr Opin Chem Biol* 9(5): 447-58.

Xiao, J. J., J. Byrd, et al. (2003). "Identification of thiols and glutathione conjugates of depsipeptide FK228 (FR901228), a novel histone protein deacetylase inhibitor, in the blood." *Rapid Commun Mass Spectrom* 17(8): 757-66.

Yoo, C. B. and P. A. Jones (2006). "Epigenetic therapy of cancer: past, present and future." *Nat Rev Drug Discov* 5(1): 37-50.

Yu, X., Z. S. Guo, et al. (2002). "Modulation of p53, ErbB1, ErbB2, and Raf-1 expression in lung cancer cells by depsipeptide FR901228." *J Natl Cancer Inst* 94(7): 504-13.

Yurek-George, A., A. R. Cecil, et al. (2007). "The first biologically active synthetic analogues of FK228, the depsipeptide histone deacetylase inhibitor." *J Med Chem* 50(23): 5720-6.

Zazopoulos, E., K. Huang, et al. (2003). "A genomics-guided approach for discovering and expressing cryptic metabolic pathways." *Nat Biotechnol* 21(2): 187-90.

Zhou, X., X. He, et al. (2005). "A novel DNA modification by sulphur." *Mol Microbiol* 57(5): 1428-38.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08148102B2). An electronic copy of the "Sequence Listing" will also be available from the USPTO upon request and payment of the fee set forth in 37 CFR 1.19(b)(3).

What is claimed is:

1. A method of making FK228 comprising growing a recombinant cell comprising exogenous polynucleotides encoding proteins DepA of SEQ ID NO: 29, DepB of SEQ ID NO: 31, DepC of SEQ ID NO: 33, DepD of SEQ ID NO: 35, DepE of SEQ ID NO: 37, DepF of SEQ ID NO: 39, DepH of SEQ ID NO: 43, and DepM of SEQ ID NO: 25, the polynucleotides operably connected to a promoter, under conditions that allow synthesis of FK228.

2. The method of claim 1, wherein the cell is a bacterium of a genus selected from the group consisting of *Chromobacterium, Pseudomonas, Escherichia, Salmonella, Burkholderia, Bifidobacterium*, or *Clostridium*.

3. The method of claim 1, further comprising introducing a polynucleotide encoding protein DepL of SEQ ID NO: 23.

4. The method of claim 1 wherein the polynucleotides comprise depA of SEQ ID NO: 28, depB of SEQ ID NO: 30, depC of SEQ ID NO: 32, depD of SEQ ID NO: 34, depE of SEQ ID NO: 36, depF of SEQ ID NO: 38, depH of SEQ ID NO: 42, and depM of SEQ ID NO: 24.

5. The method of claim 1, further comprising introducing a polynucleotide sequence encoding protein DepG of SEQ ID NO: 41.

6. The method of claim 1, further comprising introducing a polynucleotide sequence encoding protein DepI of SEQ ID NO: 45.

7. The method of claim 1, further comprising introducing a polynucleotide sequence encoding protein DepJ of SEQ ID NO: 47.

8. The method of claim 1, further comprising introducing a polynucleotide sequence encoding protein DepK of SEQ ID NO: 21.

9. The method of claim 1, further comprising introducing at least one polynucleotide sequence encoding at least one protein selected from the group consisting of DepG of SEQ ID NO: 41, DepL of SEQ ID NO: 23, DepI of SEQ ID NO: 45, DepJ of SEQ ID NO: 47, and DepK of SEQ ID NO: 21, or any combination thereof.

10. The method of claim 1 wherein the polynucleotide comprises SEQ ID NO: 1.

* * * * *